(12) United States Patent
Greco et al.

(10) Patent No.: US 7,872,044 B2
(45) Date of Patent: Jan. 18, 2011

(54) INHIBITORS OF CHYMASE

(75) Inventors: Michael Greco, Lansdale, PA (US);
Michael Hawkins, Ambler, PA (US);
Eugene Powell, Pipersville, PA (US);
Bruce E. Maryanoff, Forest Grove, PA (US)

(73) Assignee: Janssen Pharmaceutica NV (BE)

( * ) Notice: Subject to any disclaimer, the term of this patent is extended or adjusted under 35 U.S.C. 154(b) by 141 days.

(21) Appl. No.: 11/975,235

(22) Filed: Oct. 18, 2007

(65) Prior Publication Data
US 2008/0096844 A1   Apr. 24, 2008

Related U.S. Application Data

(60) Provisional application No. 60/852,604, filed on Oct. 18, 2006.

(51) Int. Cl.
*A61K 31/343* (2006.01)
*C07D 307/87* (2006.01)
*C07F 9/28* (2006.01)

(52) U.S. Cl. .................. 514/469; 549/220; 549/467
(58) Field of Classification Search ................. 549/220
See application file for complete search history.

(56) References Cited

U.S. PATENT DOCUMENTS

| 5,508,273 | A | 4/1996 | Beers et al. |
| 2005/0176769 | A1 | 8/2005 | Hawkins et al. |

FOREIGN PATENT DOCUMENTS

| EP | 0661260 | 7/1995 |
| GR | 1399089 | 5/1971 |
| WO | WO 2005/073214 A2 | 8/2005 |
| WO | WO 2005/073214 A3 | 8/2005 |

OTHER PUBLICATIONS

Rouhi, Chemical and Engineering News (2003) pp. 32-35.*
U.S. Appl. No. 11/037,938, filed Jan. 18, 2005, Hawkins et al.
Schwender et al, "1-Naphthylmethylphosphonic Acid Derivatives as Osteoclastic Acid Phosphatase Inhibitors," Bioorganic and Medicinal Chemistry Letters, 1995, pp. 1801-1806, vol. 5, No. 16, Elsevier Science, LTD, Great Britain.
Deprele et al, "A Novel and Conveneient Preparation of Hypophosphite Esters," Journal of Organo Metallic Chemistry, 2002, pp. 154-163, 643-644, Elsevier Science.
De Lombaert et al, "Non-Peptide Inhibitors of Neutral Endopeptidase 24.11 2. Design and Pharmacology Oforally Active Phosphonate Prodrugs," Bioorganic & Medicinal Chemistry Letters, 1995, pp. 151-154, vol. 5, No. 2, Elsevier Science, Ltd., Great Britain.
De Lombaert et al, "N-Phosphonomethyl Dipeptides and Their Phosphonate Prodrugs, A New Generation of Neutral Endopeptidase (NEP, EC 3.4.24.11) Inhibitors," J. Med. Chem., 1994, pp. 498-511, American Chemical Society.

Longley et al, "Chymase Cleavage of Stem Cell Factor Yields a Bioactive Soluble Product," Proc Natl Acad Science, 1997, pp. 9017-9021, vol. 94, Biochemistry, USA.
Takai et al, "Application of a Chymase Inhibitor, NK3201, for Prevention of Vascular Proliferation," Cardiovascular Drug Reviews, 2003, pp. 185-198, vol. 21, No. 3, Neva Press, USA.
Ehara et al, "Contribution of Mast Cells to the Tubulointerstitial Lesions in Iganephritis," Kidney International, 1998, pp. 1675-1683, vol. 54, International Society of Nephrology.
Okamoto et al, "Chymase Inhibitor, BCEAB, Suppressed Peritoneal Adhesion Formation in Hamster," Journal of Surgical Research, 2002, pp. 219-222, vol. 107, Elsevier Science, USA.
Yao et al, "Association Between the Expression of Mast Cell Chymase and Intraperitoneal Adhesion Formation in Mice," Journal of Surgical Research, 2000, pp. 40-44, vol. 92, Academic Press.
Paananen et al, "Proteolysis and Fusion of Low Density Lipoprotein Particles Independently Strengthen Their Binding to Exocytosed Mast Cell Granules," The Journal of Biological Chemistry, 1994, pp. 2023-2031, vol. 269, No. 3, The American Society for Biochemistry and Molecular Biology, Inc., USA.
Lindstedt et al, "Chymase in Exocytosed Rat Mast Cell Granules Effectively Proteolyzes Apolipoprotein Al-Containing Lipoproteins, so Reducing the Cholesterol Efflux-Inducing Ability of Serum and Aortic Intimal Fluid," J. Clin Invest., 1996. pp. 2174-2182, vol. 97, No. 10, The American Society for Clinical Investigation, Inc.
Matsumoto et al, "Chymase Inhibition Prevents Cardiac Fibrosis and Improves Disatolic Dysfunction in the Progression of Heart Failure," Circulation, 2003, pp. 2555-2558, vol. 107.
Katritzky et al, "A One-Pot Procedure for the Preparation of Phosphoic Acids From Alkyl Halides," Organic Preparations and Procedures Int., 1990, pp. 209-213, vol. 22, No. 2.
Belley et al, "Synthesis of the Nanomolar Photoaffinity $GABA_b$ Receptor Ligand CGP 71872 Reveals Diversity in the Tissue Distribution of $GABA_b$ Receptor Forms," Bioorganic & Medicinal Chemistry, 1999, pp. 2697-2704, 7, Elsevier Science Ltd.
Deprele et al, "Palladium-Catalyzed Hydrophosphinylation of Alkenes and Alkynes," J. Am. Chem. Soc., 2002, pp. 9386-9387, American Chemical Society.

(Continued)

*Primary Examiner*—Rebecca L Anderson
*Assistant Examiner*—Shawquia Young
(74) *Attorney, Agent, or Firm*—Yuriy P. Stercho

(57) ABSTRACT

The present invention is directed to a compound of Formula (I):

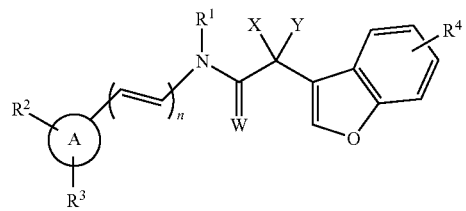

or an enantiomer, diastereomer, polymorph or pharmaceutically acceptable salt thereof and methods for preparing said compounds and compositions, intermediates and derivatives thereof, and methods for treating inflammatory or serine protease mediated disorders.

19 Claims, No Drawings

OTHER PUBLICATIONS

Henke et al, "Optimization of 3-(1H-Indazol-3-Ylmethyl)—1.5 Benzodiazepines as Potent, Orally Active CCK-A Agonists," J. Med. Chem, 1997, pp. 2706-2725, vol. 40, American Chemical Society.
Steininger et al, Chem Ber, 1963, pp. 3184-3194.
Froestl et al, "Phosphonic Acid Analyogues of GABA 1. New Potent and Selective $GABA_b$ Agonists," j med. Chem.., 1995, pp. 3297-3312, vol. 38.
Yamashiro et al, "Distributino of Intrahepatic Mast Cells in Various Hepatobiliary Disorders," Virchows Arch, 1998, pp. 471-479, vol. 433.
Design of Prodrugs, Ed. H. Bundgaard, Elsevier, 1985.
Protective Groups in Organic Cheemistry, Ed. J.F.W.McOmie, Plenum Press, 1973.
T.W. Greene & P.G.M. Wuts, Protective Groups in Organic Synthesis, John Wiley & Sons, 1991.
Garabadzhiu et al, "Reactions of Perfluoroalkyl Iodides With Phosphorus (III) Esters, V. Kinetics and Mechanism of the Reactions of Heptafluoropropyl Iodide With Ethylphosphonous Esters," Journal of General Chemistry USSR—Eng Translation Version 1981, 1905-10, ISSN 00221279, The British Library.
Depaulis et al, "Novel Autocrine and Paracrine Loops of the Stem Cell Factor/Chymase Network," int arch allergy immunol, 1999, pp. 422-425, vol. 118.
Hara et al, "Evidence for a Role of Mast Cells in the Evolution to Confestive Heart Failure," J. Exp. Med., 2002, pp. 375-381, vol. 195, No. 3.
Lucas et al, "Formation of Abdominal Adhesions is Inhibited by Antibodies to Transforming Growth Factor-β1," Journal of Surgical Research, 1996, pp. 135-138, vol. 65, Academic Press.
Gotis-Graham et al.,"Mast Cell Responses in Rheumatoid Synovium: Association of the MC sub TC subset with Matrix Turnover and Clinical Progession," 1997, pp. 479-489, vol. 40 (3), American College of Rheumagtology.
Gould et al., "Salt Selection for basic drugs,"International Journal of Pharmaceutics, 1986, pp. 201-217, vol. 33, Elsevier Science Publishers B.V.
Graham et al., "Topically Active Carbonic Anhydrase Inhibitors," J Med. Chem, 1989, pp. 2548-2554, vol. 32, No. 12, American Chemical Society.
Egfange et al., "Modified Ibogaine Fragments: Synthesis and Preliminary Pharmacological characterization of 3-Ethyl-5-phenly-1,2,3,4,5,6- hexahydroazepino[4,5-b] benzothiophenes," J Med Chem, 1998, pp. 4486-4491, vol. 41, American Chemical Society.
Ple et al., "Synthesis of Substituted Benzo [b]thiophenes by Acid-Catalyzed Cyclizagtion of Thiophenylacetals and Ketones," J. Heterocyclic Chem, 1988, pp. 1271, 25.
Steininger, "Uber die Herstellung von Bis-phosphiinigsaureestern and anderer Bix-phosphorverbindungen," Chem Berg, 1963, pp. 3184-3194, 96.
Cory et al, "Extended Chains of Six-Membered Rings 1. Model Studies and Key Intermediates," Synthetic Communications, 1994, pp. 799-807, vol. 24, No. 6 Marcel Dekker, Inc.
Michele Rebound-Ravaux et al, Journal De La Societe De Biologie, ISSN 1295-0661, 2001, pp. 143-150, vol. 195, No. 2.
Matsumoto et al., "Chymase Inhibition Prevents Cardiac Fibrosis and Improves Diastolic Dysfunction in the Progression of heart Failure," Circulation, pp. 2555-2558.
Denney et al., "Isomeric five-Membered ring Phophites and Phosphates" Journal of the American Chemical society, 1969, pp. 6838-6841, vol. 91, 24.
Grasa et al., "Amination Reactions of Aryl halides with Nitrogen-Containing reagents Mediated by Palladium/Imidazolium salts Systems," J Org Chem, pp. 7729-7737, vol. 66.
Belley et al., "Synthesis of the Nanomolar Photoaffinity $GABA_B$ Receptor Ligand CGP 71872 Reveals Diveristy in the Tissue distribution of $GFABA_B$ receptor forms," Biorganic and Medicinal Chemistry, 1999, pp. 2697-2704, vol. 7, Elsevier Science Ltd.

Martinez et al, "New 3-[4-(aryl)piperazin-1-yl]-1-(benzo[b]thiophen-3-yl) propane derivatives with dual action at $5-HT_{1A}$ serotonin receptors and serotonin transporter as a new class of antidepressants," Eur J. Med Chem, 2001, pp. 55-61, vol. 36, Elsevier.
Berge et al., Pharmaceutical Salts, Journal of Pharmaceutical Sciences, 1977, pp. 1-19, vol. 66, No. 1.
Abraham et al., "Pharmacology of Allergen-Induced early and Late Airway responses and Antigen-Induced Hyperresponsiveness in allergic sheep," Pulmonary Pharmacology, 1989, pp. 33-40, vol. 2, Longman Group UK Ltd.
Borch et al, "The Cyanohydridoborate Anion as A Selective Reducing Agent," Journal of the American Chemical Society, 1971, pp. 2897-2904, vol. 93, No. 12 Cyanohydriodoborate Anion.
Taft et al, "Fluorine Nuclear Magnetic Resonance Shielding in meta-Substituted Fluobenzenes. The effect of solvent on the Inductive Order," Journal of the American Chemical society, 1963, vol. 85, No. 6 pp. 711-716.
Seto et al, Molecular self-Assembly through Hydrogen bonding: Aggregation of Five Molecules to form a Discrete Supramolecular Structure.
Collins et al, "Organophosphorus Compounds, XIX+Synthesis of 2,3 Dihydro-1H-1,2-benzaza-phosphole 2-oxides, variously substituted on nitrogen and phosphorus, by N-P Cyclization of Zqitterionic Intermediates," Aust J. chem., 1983, pp. 2517-2536, No. 36.
Greco et al., "Discovery of Potent, Selective, Orally Active, Nonpeptide Inhibitors of human mast Cell Chymase," J Med Chem, 2007, pp. 1727-1730, vol. 50, American Chemical Society.
Maryanoff et al, "Protease Inhibitors for treating pulmonary inflammatory disorders: focus on Chymase and cathepsin G, "Abstracts of Papers, $234^{th}$ ACS National Meeting, Aug. 19-23, 2007. Medi-247, Coden: 69JNR2 An 2007:883608. Caplus.
Hawkins et al, "Structure-based design of serine protease inhibitors: Discovery of selective Chymase inhibitors containing a novel beta-amidophosphonic acid recognition motif." Abstracts of Papers, $232^{nd}$ ACS National Meeting, San Francisco, CA United States, Sep. 10-14, 2006 (2006) Orgn-623. Coden: 691hrd an 2006;862763 Caplus.
Hawkins et al, Structure-based design of serine protease inhibitors: Discovery of selective Chymase inhibitors containing a novel β-amidophosphonic acid recognition motif,: Abstracts of Papers, $230^{th}$ ACS National Meeting, Washington, DC, United States, Aug. 28-Sep. 1 2005 (2005) Medi-336, Coden: 69hfcl an2005:739844 Caplus.
Goodman & Gilman Pharmacological Basis of Therapeutics, 1996, $9^{th}$ Ed., vol. 1 47, 58, McGraw Hill.
Tempest et al,"MCC/SnAr methodology. Part 1", Tetrahedron Lett., vol. 42, 2001, pp. 4963-4968, XP002336083 compound 28.
Aoyama, Yasunori et al., Synthesis and Structure-Activity relationships of a New Class of 1-Oxacephem-based human Chymase Inhibitors: bioorganic & Medicinal Chemistry letters 10 (2000) pp. 2397-2401 XP-002336087.
Bertrand, Jay A. et al., Inhibition of Trypsin and Thrombin by Amino(4-amidinophenyl)methanephosphonate Diphenyl Ester Derivatives: X-Ray Structures and Molecular Models: Biochemistry 35 (1996) pp. 3147-3155 XP-002336085.
Fukami, H. et al Chymase: Its Pathophysiological Roles and Inhibitors: Current Pharmaceutical Design 4 (1998) pp. 439-453 XP-000885575.
Greco, Michael N. et al., Nonpeptide Inhibitors of Cathespin G. Optimization of a Novel β-Ketophosphonic Acid Lead by Structure-Based Drug Design: J. Am. Chem. Soc. 124 (2002) pp. 3810-3811 XP002336084.
Lachkova, Victoria et al, Interaction Between Phenylmethanephosphonic Acid Diethy Ester and Isothiocyanates: Phosphorus, Sulfur and Silicon 48 (1990) pp. 227-233 0X009050625.
Oleksyszyn, J. et al., Irreverisible Inhibition of Serine Proteases by Peptide Derivatives of (a-Aminoalkyl) Phosphonate Diphenyl esters: 30 (1991) pp. 485-493 XP002336086.

* cited by examiner

INHIBITORS OF CHYMASE

CROSS REFERENCE TO RELATED APPLICATIONS

This present application claims benefit of U.S. Provisional Patent Application Ser. No. 60/852,604, filed Oct. 18, 2006, which is incorporated herein by reference in its entirety and for all purposes.

FIELD OF THE INVENTION

The present invention relates to certain novel compounds, methods for preparing compounds, compositions, intermediates and derivatives thereof and methods for treating inflammatory or serine protease mediated disorders. More particularly, the compounds of the present invention are serine protease inhibitors useful for treating inflammatory or serine protease mediated disorders.

BACKGROUND OF THE INVENTION

Serine proteases represent a broad class of proteolytic enzymes that are involved in physiological processes such as blood coagulation, complement activation, phagocytosis and turnover of damaged cell tissue. Human chymase (EC.3.4.21.39) is a glycosylated monomeric chymotrypsin-like serine protease (MW=30 kDa) localized mainly in mast cell secretory granules. Chymase is thought to have a variety of functions, including degradation of extracellular matrix proteins, cleavage of angiotensin I to angiotensin II (except in the rat), and activation of matrix proteases and cytokines. Endogenously, chymase is regulated by the serpins α1-antichymotrypsin and α1-protease.

Although the precise patho-physiological roles of chymase have yet to be determined, chymase has been implicated in microvascular leakage, neutrophil accumulation, the stimulation of mucus secretion, and the modulation of cytokines. A potent, chymase-selective inhibitor may be indicated in inflammatory or serine protease (such as mast cell) mediated diseases such as asthma, pulmonary inflammation, and chronic obstructive pulmonary diseases (COPD). Because chymase can play a role in the generation of cardiac and vascular wall angiotensin II, an inhibitor may have potential use as an antihypertensive treatment for vascular wall injury and inflammation (atherosclerosis/restenosis), as well as cardiac hypertrophy. Thus, small molecule inhibitors of chymase are likely to represent useful therapeutic agents.

U.S. Pat. No. 5,508,273 to Beers, et al. and *Bioorganic & Med. Chem. Lett.*, 1995, 5 (16), 1801-1806 describe phosphonic acid compounds useful in treating bone wasting diseases.

United States Patent Application 2005/0176769 describes aryl and heteroaryl substituted phosphinic and phosphonic acid compounds useful in treating Inflammatory and serine protease mediated diseases.

Accordingly, it is an object of the present invention to provide phosphonic acid and phosphinic acid compounds that are serine protease inhibitors, in particular, inhibitors of chymase, useful for treating inflammatory or serine protease mediated disorders. It is another object of the invention to provide a process for preparing phosphonic or phosphinic acid compounds, compositions, intermediates and derivatives thereof. It is a further object of the invention to provide methods for treating inflammatory or serine protease mediated disorders.

SUMMARY OF THE INVENTION

The present invention is directed to a compound of Formula (I):

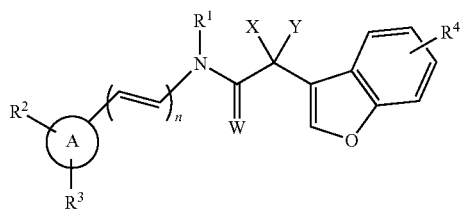

and enantiomers, diastereomers, polymorphs or pharmaceutically acceptable salts thereof, wherein Ring A, $R^1$, $R^2$, $R^3$, $R^4$, n, W, X and Y are as defined herein.

The present invention provides phosphonic acid and phosphinic acid compounds that are serine protease inhibitors.

An example of a serine protease inhibited by a compound of the present invention is chymase.

Another example of the present invention includes chymase inhibitor compounds useful for treating inflammatory or serine protease mediated disorders.

The present invention further provides a process for preparing phosphonic or phosphinic acid compounds, compositions, intermediates and derivatives thereof.

The present invention is also directed to a method for treating inflammatory or serine protease mediated disorders in a patient in need thereof comprising administering to the patient an effective amount of a compound of Formula (I).

DETAILED DESCRIPTION OF THE INVENTION

The present invention is directed to a compound of Formula (I):

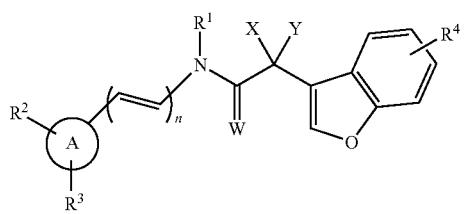

wherein $R^1$ is selected from the group consisting of hydrogen and $C_{1-4}$alkyl;

Ring A is selected from the group consisting of aryl, heteroaryl, benzo fused heterocyclyl, cycloalkyl and benzo fused cycloalkyl;

$R^2$ is one, two or three substituents independently selected from the group consisting of hydrogen, $C_{1-6}$alkyl, $C_{2-6}$alkenyl, $C_{2-6}$alkynyl, $C_{1-6}$alkoxy, —$OCH_2$—$C_{2-6}$alkenyl, $C_{1-6}$alkylthio, —$OCF_3$, —$NH_2$, —$NH(C_{1-6})$alkyl, —$N(C_{1-6})$dialkyl, aryl, heteroaryl, aryloxy, heteroaryloxy, halogen, hydroxy and nitro, wherein, $R^2$ is optionally oxo when Ring A is heteroaryl or benzo fused heterocyclyl, wherein any aryl-containing substituent of $R^2$ is optionally substituted with a substituent independently selected from the group consisting of $C_{1-6}$alkyl, $C_{1-6}$alkoxy, $C_{2-6}$alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy and nitro, and wherein any of the foregoing $C_{1-6}$alkyl, $C_{2-6}$alkenyl or $C_{1-6}$alkoxy containing substituents of $R^2$ are optionally substituted with a substituent independently selected from the group consisting of —$NR^{11}R^{12}$, aryl, heteroaryl, one, two or three halogen atoms and hydroxy;

$R^{11}$ and $R^{12}$ are independently hydrogen; $C_{1-6}$alkyl optionally substituted with hydroxy, aryl, —C(=O)$C_{1-4}$alkoxy, or —$NR^{15}R^{16}$; or aryl;

$R^{15}$ and $R^{16}$ are substituents independently selected from the group consisting of hydrogen, $C_{1-6}$alkyl and aryl; optionally, $R^{15}$ and $R^{16}$ are each taken together with the atoms to which they are attached to form a ring of five to seven members;

$R^3$ is one, two or three substituents independently selected from the group consisting of hydrogen, $C_{1-6}$alkyl, $C_{2-6}$alkenyl, $C_{2-6}$alkynyl, $C_{1-6}$alkoxy, $C_{1-6}$alkylthio, —$OCF_3$, —$OCH_2(C_{2-6})$alkenyl, —$NH_2$, —$NH(C_{1-6})$alkyl, —$N(C_{1-6})$dialkyl, —NHC(=O)Cy, —$N(C_{1-6}$alkyl)C(=O)Cy, —(NC(=O))$_2NH_2$, —C(=O)$C_{1-4}$alkoxy, —C(=O)$NR^{17}R^{18}$, —C(=O)NHcycloalkyl, —C(=O)N($C_{1-6}$alkyl)cycloalkyl, —C(=O)NHCy, —C(=O)N($C_{1-6}$alkyl)Cy, —OC(=O)Cy, —C(=O)$C_{1-6}$alkyl, —OC(=O)$NR^{19}R^{20}$, —C(=O)Oaryl, —C(=O)Oheteroaryl, —$CO_2H$, ureido, halogen, hydroxy, nitro, cyano, aryl, heteroaryl, heteroaryloxy and aryloxy, wherein any of the foregoing $C_{1-6}$alkyl or $C_{1-6}$alkoxy containing substituents of $R^3$ are optionally substituted with one, two or three substituents independently selected from the group consisting of —$NR^{21}R^{22}$, —NH(cycloalkyl), —N($C_{1-6}$alkyl)(cycloalkyl), —NHCy, —N($C_{1-6}$alkyl)Cy, —NHC(O)—$C_{1-6}$alkyl-$C_{1-6}$alkoxy, aryl, heteroaryl, hydroxy, halogen, —C(=O)$NR^{23}R^{24}$, —OC(=O)$NR^{25}R^{26}$, —C(=O)$C_{1-4}$alkoxy and —C(=O)Cy, wherein any of the foregoing $C_{2-6}$alkenyl and $C_{2-6}$alkynyl containing substituents of $R^3$ are optionally substituted with aryl or —C(=O)$NR^{27}R^{28}$, and wherein the aryl, heteroaryl and cycloalkyl substituents of $R^3$ are optionally substituted with one, two or three substituents independently selected from $R^{14}$;

$R^{14}$ is independently hydrogen, $C_{1-6}$alkyl, $C_{1-6}$alkoxy, $C_{2-6}$alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy, or nitro;

wherein each of the $C_{1-6}$alkyl- or $C_{1-6}$alkoxy-containing substituents of $R^{14}$ is optionally substituted on a terminal carbon atom with a substituent selected from —$NR^{29}R^{30}$, aryl, heteroaryl, one, two or three halogen atoms, or hydroxy;

$R^{17}$, $R^{18}$, $R^{19}$, $R^{20}$, $R^{21}$, $R^{22}$, $R^{23}$, $R^{24}$, $R^{25}$ and $R^{26}$ are substituents independently selected from the group consisting of hydrogen, $C_{1-6}$alkyl and aryl, wherein $C_{1-6}$alkyl and aryl are each optionally substituted with hydroxy, aryl, aryloxy, —C(=O)-aryl, —C(=O)$C_{1-4}$ alkoxy, $NH_2$, —$NH(C_{1-6}$alkyl), or —$N(C_{1-6})$dialkyl; optionally, $R^{17}$ and $R^{18}$, $R^{19}$ and $R^{20}$, $R^{21}$ and $R^{22}$, $R^{23}$ and $R^{24}$ or $R^{25}$ and $R^{26}$ are each taken together with the atoms to which they are attached to form a ring of five to seven members;

$R^{27}$ and $R^{28}$ are independently hydrogen; $C_{1-6}$alkyl optionally substituted with hydroxy, aryl, —C(=O)$C_{1-4}$alkoxy, $NH_2$, —$NH(C_{1-6}$alkyl), or —$N(C_{1-6})$dialkyl; or aryl; optionally, $R^{27}$ and $R^{28}$ are each taken together with the atoms to which they are attached to form a ring of five to seven members;

$R^{29}$ and $R^{30}$ are independently hydrogen, $C_{1-6}$alkyl or aryl, wherein $C_{1-6}$alkyl is optionally substituted with hydroxy, aryl, —C(=O)$C_{1-4}$alkoxy, $NH_2$, —$NH(C_{1-6}$alkyl), or —$N(C_{1-6})$dialkyl, and, optionally, $R^{29}$ and $R^{30}$ are each taken together with the atoms to which they are attached to form a ring of five to seven members;

Cy is a heterocyclyl optionally substituted with a substituent selected from the group consisting of oxo, $C_{1-6}$alkyl, —$C_{1-6}$ alkylC(=O)$C_{1-6}$alkyl, —$C_{1-6}$alkylC(=O)$C_{1-6}$alkoxy, —$C_{1-6}$alkyl-aryl, —$C_{1-6}$alkylC(=O)aryl, —C(=O)($C_{1-6}$)alkyl, —C(=O)($C_{1-6}$)alkoxy, —C(=O)aryl, —$SO_2$aryl, aryl, heteroaryl and heterocyclyl, wherein the aryl portion of any aryl-containing substituent of Cy is optionally substituted with one, two or three substituents independently selected from the group consisting of $C_{1-6}$alkyl, $C_{1-6}$alkoxy, $C_{1-6}$alkylthio, halogen, hydroxy, $NH_2$, —$NH(C_{1-6}$alkyl) and —$N(C_{1-6})$dialkyl, and wherein heterocyclyl is optionally substituted with aryl, one, two or three halogen atoms, or one, two or three oxo substituents; and heterocyclyl is optionally spiro-fused to said Cy;

n is 0 or 1;

W is O or S;

X is hydrogen or $C_{1-3}$alkyl;

Y is independently selected from the group consisting of $C_{1-6}$alkyl substituted with —$OSO_2NH_2$ or hydroxy; $SO_3H$, $CO_2H$, heteroaryl, —OC(=O)$NH_2$ and P(=O)$OR^5R^6$; provided that when Y is $CO_2H$, Ring A must be a bicyclic ring system;

$R^5$ is selected from the group consisting of hydrogen, $C_{1-6}$alkyl and aryl, wherein $C_{1-6}$alkyl is optionally substituted with $NH_2$, —NH($C_{1-6}$)alkyl, —N($C_{1-6}$)dialkyl, 1,3-dioxolan-2-yl, $C_{1-6}$alkylcarbonyloxy-, $C_{1-6}$alkoxycarbonyloxy-, $C_{1-6}$alkylcarbonylthio-, ($C_{1-6}$)alkylaminocarbonyl-, di($C_{1-6}$)alkylaminocarbonyl-, one, two or three halogen atoms, or hydroxy, and wherein aryl is optionally substituted with $C_{1-6}$alkyl, $C_{1-6}$alkoxy, $C_{1-6}$alkylthio, $C_{2-6}$alkenyl, —$NH_2$, —$NH(C_{1-6})$alkyl, —$N(C_{1-6})$dialkyl, aryl, heteroaryl, aryloxy, heteroaryloxy, halogen, hydroxy, or nitro, and, optionally, when $R^6$ is $C_{1-8}$alkoxy, $R^5$ and $R^6$ are each taken together with the atoms to which they are attached to form a 5-8 membered monocyclic ring;

$R^6$ is selected from the group consisting of $C_{1-8}$alkyl, $C_{1-8}$alkoxy, $C_{2-8}$alkenyl, heteroaryl, aryl and hydroxy, wherein $C_{1-8}$alkyl, $C_{1-8}$alkoxy and $C_{2-8}$alkenyl are optionally substituted with a substituent selected from the group consisting of $C_{1-6}$alkoxy, aryl, heterocyclyl, heteroaryl, $NH_2$, —$NH(C_{1-6})$alkyl, —$N(C_{1-6})$dialkyl, $C_{1-6}$alkylcarbonyloxy-, $C_{1-6}$alkylcarbonylthio-, $C_{1-6}$alkoxycarbonyloxy-, ($C_{1-6}$)alkylaminocarbonyl-, di($C_{1-6}$)alkylaminocarbonyl-, one, two or three halogen atoms and hydroxy, wherein when $R^6$ is $C_{1-8}$alkyl, said $C_{1-8}$alkyl is optionally substituted with halogen selected from up to three chlorine atoms or up to seven fluorine atoms, and wherein the heteroaryl and aryl substituents of $R^6$ are optionally substituted with a substituent independently selected from the group consisting of $C_{1-6}$alkyl, $C_{1-6}$alkoxy, $C_{2-6}$alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy and nitro;

$R^4$ is one, two or three substituents selected from the group consisting of hydrogen, $C_{1-6}$alkyl, $C_{2-6}$alkenyl, $C_{1-6}$alkoxy, $C_{1-6}$alkylthio, aryl($C_{1-6}$)alkyl, aryl($C_{2-6}$)alkenyl, halogen, hydroxy, —C(=O)Cy, —C(=O)$NR^{31}R^{32}$, aryl, —$CO_2H$, oxo and cyano, wherein $C_{1-6}$alkyl, $C_{2-6}$alkenyl and $C_{1-6}$alkoxy are each optionally substituted with —$NR^{33}R^{34}$, aryl, heteroaryl, cycloalkyl, one, two or three halogen atoms, or hydroxy, and wherein aryl and heteroaryl are each optionally substituted with a substituent independently selected from the group consisting of $C_{1-6}$alkyl, $C_{1-6}$alkoxy, $C_{2-6}$alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, one, two or three halogen atoms, hydroxy and nitro;

$R^{31}$, $R^{32}$, $R^{33}$ and $R^{34}$ are substituents independently selected from the group consisting of hydrogen, $C_{1-6}$alkyl and aryl, wherein $C_{1-6}$alkyl is optionally substituted with hydroxy, aryl, —C(=O)$C_{1-4}$alkoxy, $NH_2$, —$NH(C_{1-6}$alkyl), or —$N(C_{1-6})$dialkyl, and, optionally, $R^{31}$ and $R^{32}$ or $R^{33}$ and $R^{34}$ are each taken together with the atoms to which they are attached to form a ring of five to seven members;

and enantiomers, diastereomers, polymorphs or pharmaceutically acceptable salts thereof.

Illustrative of the invention is a pharmaceutical composition comprising a pharmaceutically acceptable carrier and any of the compounds described above.

An illustration of the invention is a pharmaceutical composition made by mixing any of the compounds described above and a pharmaceutically acceptable carrier.

Illustrating the invention is a process for making a pharmaceutical composition comprising mixing any of the compounds described above and a pharmaceutically acceptable carrier.

The present invention is also directed to methods for producing the instant compounds and pharmaceutical compositions and medicaments thereof.

The present invention is further directed to methods for treating or ameliorating an inflammatory or serine protease-mediated disorder. In particular, the method of the present invention is directed to treating or ameliorating an inflammatory or serine protease (such as chymase) mediated disorder such as, but not limited to, allergic rhinitis, viral rhinitis, asthma, chronic obstructive pulmonary diseases, bronchitis, pulmonary emphysema, acute lung injury, psoriasis, arthritis, reperfusion injury, ischemia, hypertension, hypercardia myocardial infarction, heart failure damage associated with myocardial infarction and cardiac hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars, rheumatoid arthritis, bullous pemphiguoid and atherosclerosis. Additionally, these compounds can be used for modulating wound healing and remodeling (e.g., cardiac hypertrophy) as well as immune modulation.

An embodiment of the present invention includes a method for treating or ameliorating an inflammatory or serine protease mediated disorder selected from the group consisting of allergic rhinitis, asthma and heart failure damage associated with myocardial infarction and cardiac hypertrophy.

An embodiment of the present invention includes compounds of Formula (I) wherein $R^1$ is selected from the group consisting of hydrogen and $C_{1-4}$alkyl.

Examples of the present invention include compounds of Formula (I) wherein $R^1$ is hydrogen.

An embodiment of the present invention includes compounds of Formula (I) wherein Ring A is selected from the group consisting of aryl, heteroaryl, benzo fused heterocyclyl and benzo fused cycloalkyl.

An embodiment of the present invention includes compounds of Formula (I) wherein Ring A is selected from the group consisting of heteroaryl, benzo fused heterocyclyl, or aryl.

An embodiment of the present invention includes compounds of Formula (I) wherein Ring A is a bicyclic Ring $a^1a^2$ of the formula:

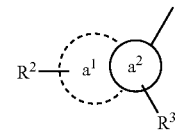

wherein the $a^1$ portion of said Ring $a^1a^2$ is optionally substituted with $R^2$; and the $a^2$ portion is optionally substituted with $R^3$.

An embodiment of the present invention includes compounds of Formula (I) wherein the $a^2$ portion of Ring $a^1a^2$ is an aromatic ring.

An embodiment of the present invention includes compounds of Formula (I) wherein Ring A is selected from the group consisting of naphthyl, benzothiazolyl, benzothiophenyl, quinolinyl, isoquinolinyl, dihydronaphthyl, indanyl, tetrazolinyl and benzodioxolyl when n is equal to zero; and Ring A is phenyl, pyridin-2-yl, or pyridin-3-yl when n is equal to one.

In embodiments of the present invention wherein, for compounds of Formula (I), a bicyclic ring system is used for Ring A, the $a^2$ ring will be aromatic. For example, Ring A is selected from the group consisting of naphthyl, benzothiazolyl and benzothiophenyl, when n is equal to zero, and Ring A is selected from phenyl, pyridin-2-yl and pyridin-3-yl when n is equal to one.

Embodiments of the present invention include compounds of Formula (I) wherein n is 0.

Examples of the present invention includes compounds of Formula (I) wherein Ring A is naphthyl and n is 0.

Embodiments of the present invention include compounds of Formula (I)
wherein $R^2$ is one, two or three substituents independently selected from the group consisting of hydrogen, $C_{1-6}$alkyl, $C_{1-6}$alkoxy, —$NH_2$, —$NH(C_{1-6}$alkyl), —$N(C_{1-6})$dialkyl, aryl, heteroaryl, halogen, hydroxy and nitro, and
wherein $C_{1-6}$alkyl and $C_{1-6}$alkoxy are optionally substituted with a substituent selected from —$NR^{11}R^{12}$, aryl, heteroaryl, one, two or three halogen atoms and hydroxy.

Embodiments of the present invention include compounds of Formula (I) wherein $R^2$ is a substituent independently selected from the group consisting of hydrogen, $C_{1-4}$alkyl, $C_{1-4}$alkoxy, hydroxy, halogen and —$NH_2$.

Embodiments of the present invention include compounds of Formula (I) wherein $R^2$ is hydrogen, $C_{1-4}$alkyl, halogen, or —$NH_2$.

Examples of the present invention include compounds of Formula (I) wherein $R^2$ is hydrogen.

Embodiments of the present invention include compounds of Formula (I)
wherein $R^3$ is one, two or three substituents independently selected from the group consisting of hydrogen, $C_{1-6}$alkyl, $C_{2-6}$alkenyl, $C_{1-6}$alkoxy, —OCH$_2$($C_{2-6}$)alkenyl, NH$_2$, —NH($C_{1-6}$alkyl), —N($C_{1-6}$)dialkyl, —NHC(=O)Cy, —N($C_{1-6}$alkyl)C(=O)Cy, —C(=O)$C_{1-4}$alkoxy, —C(=O)NR$^{17}$R$^{18}$, —C(=O)NHcycloalkyl, —C(=O)N($C_{1-6}$alkyl)cycloalkyl, —C(=O)NHCy, —C(=O)N($C_{1-6}$alkyl)Cy, —C(=O)Cy, —OC(=O)NR$^{19}$R$^{20}$, halogen, hydroxy, nitro, cyano, aryl and aryloxy,
wherein $C_{1-6}$alkyl and $C_{1-6}$alkoxy are optionally substituted with one, two or three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, aryl, heteroaryl, halogen, —C(=O)NR$^{23}$R$^{24}$, —OC(=O)NR$^{25}$R$^{26}$—C(=O)($C_{1-4}$)alkoxy and —C(=O)Cy,
wherein $C_{2-6}$alkenyl is optionally substituted on a terminal carbon with aryl or —C(=O)NR$^{27}$R$^{28}$, and
wherein aryl and cycloalkyl are optionally substituted with one, two or three substituents independently selected from R$^{14}$.

Embodiments of the present invention include compounds of Formula (I)
wherein $R^3$ is one, two or three substituents independently selected from the group consisting of hydrogen, $C_{1-6}$alkyl, $C_{1-6}$alkoxy, —NR$^{19}$R$^{20}$, —NHC(=O)Cy, —C(=O)NR$^{17}$R$^{18}$, —C(=O)NHcycloalkyl, —C(=O)N($C_{1-6}$alkyl)cycloalkyl, halogen and aryl,
wherein $C_{1-6}$alkyl and $C_{1-6}$alkoxy are optionally substituted on a terminal carbon atom with one, two or three fluorine atoms, —NH$_2$, —NHCy, or —N($C_{1-4}$alkyl)Cy, and
wherein aryl and cycloalkyl are optionally substituted with a group independently selected from R$^{14}$.

Embodiments of the present invention include compounds of Formula (I) wherein $R^3$ is one, two or three substituents independently selected from hydrogen, trifluoromethyl, $C_{1-4}$alkoxy optionally substituted with one, two or three fluorine atoms, —NH$_2$, —NHC(=O)Cy, or halogen.

Embodiments of the present invention include compounds of Formula (I)
wherein when $R^3$ is NHC(=O)Cy, then Cy is preferably piperidinyl optionally substituted with a substituent selected from the group consisting of $C_{1-4}$alkyl, $C_{1-4}$alkylC(=O)$C_{1-4}$alkyl, —$C_{1-4}$alkylC(=O)$C_{1-4}$alkoxy, $C_{1-4}$alkylC(=O)aryl, —C(=O)($C_{1-4}$)alkyl, —C(=O)($C_{1-4}$)alkoxy, —C(=O)aryl, —SO$_2$aryl, aryl, heteroaryl and heterocyclyl,
wherein aryl and the aryl portion of the $C_{1-4}$alkylC(=O)aryl, —C(=O)aryl and —SO$_2$aryl are each optionally substituted with one, two or three substituents independently selected from the group consisting of $C_{1-4}$alkyl, $C_{1-4}$alkoxy, halogen, hydroxy, NH$_2$, —NH($C_{1-6}$alkyl) and —N($C_{1-4}$)dialkyl, and
wherein heterocyclyl is optionally substituted with aryl, one, two or three halogen atoms, or one oxo substituent.

Embodiments of the present invention include compounds of Formula (I) wherein $R^3$ is hydrogen, trifluoromethyl, one or two fluorine atoms, chloro, methoxy, trifluoromethoxy, or NH$_2$.

Examples of the present invention include compounds of Formula (I) wherein $R^3$ is hydrogen.

Examples of the present invention include compounds of Formula (I) wherein W is O.

Embodiments of the present invention include compounds of Formula (I) wherein X is $C_{1-3}$alkyl.

Examples of the present invention include compounds of Formula (I) wherein X is hydrogen.

Examples of the present invention include compounds of Formula (I) wherein $R^1$, $R^2$, $R^3$ and X are each hydrogen and W is O.

Embodiments of the present invention include compounds of Formula (I)
wherein Y is independently selected from a group consisting of $C_{1-3}$alkyl, SO$_3$H, CO$_2$H, heteroaryl, —OC(=O)NH$_2$ and P(=O)OR$^5$R$^6$, and
wherein $C_{1-3}$alkyl is substituted with a substituent selected from the group consisting of —OSO$_2$NH$_2$ and hydroxy.

Examples of the present invention include compounds of Formula (I) wherein Y is independently SO$_3$H or P(=O)OR$^5$R$^6$.

Examples of the present invention include compounds of Formula (I) wherein Y is P(=O)OR$^5$R$^6$.

Embodiments of the present invention include compounds of Formula (I)
wherein $R^5$ is selected from the group consisting of hydrogen; $C_{1-6}$alkyl and aryl,
wherein $C_{1-6}$alkyl is optionally substituted with NH$_2$, —NH($C_{1-6}$)alkyl, —N($C_{1-6}$)dialkyl, $C_{1-6}$alkylcarbonyloxy-, $C_{1-6}$alkoxycarbonyloxy-, $C_{1-6}$alkylcarbonylthio-, ($C_{1-6}$)alkylaminocarbonyl-, di($C_{1-6}$)alkylamino-carbonyl-, one, two or three halogen atoms, or hydroxy, and
wherein aryl is optionally substituted with $C_{1-6}$alkyl, $C_{1-6}$alkoxy, $C_{1-6}$alkylthio, $C_{2-6}$alkenyl, —NH$_2$, —NH($C_{1-6}$)alkyl, —N($C_{1-6}$)dialkyl, aryl, heteroaryl, aryloxy, heteroaryloxy, halogen, hydroxy, or nitro; optionally, when $R^6$ is $C_{1-8}$alkoxy, $R^5$ and $R^6$ are each taken together with the atoms to which they are attached to form a 5-8 membered monocyclic ring.

Embodiments of the present invention include compounds of Formula (I)
wherein $R^5$ is selected from the group consisting of hydrogen, $C_{1-6}$alkyl and aryl,
wherein $C_{1-6}$alkyl is optionally substituted with $C_{1-6}$alkylcarbonyloxy-, $C_{1-6}$alkoxycarbonyloxy-, $C_{1-6}$alkyl-carbonylthio-, ($C_{1-6}$)alkylaminocarbonyl-, di($C_{1-6}$)alkylaminocarbonyl-, one, two or three halogen atoms, or hydroxy and, optionally, when $R^6$ is $C_{1-8}$alkoxy, $R^5$ and $R^6$ are each taken together with the atoms to which they are attached to form a 6-7 membered monocyclic ring.

Embodiments of the present invention include compounds of Formula (I) wherein $R^5$ is hydrogen or $C_{1-6}$alkyl optionally substituted with $C_{1-6}$alkylcarbonyloxy-, $C_{1-6}$alkoxycarbonyloxy-, $C_{1-6}$alkylcarbonylthio-, ($C_{1-6}$)alkylaminocarbonyl-, or di($C_{1-6}$)alkylaminocarbonyl-, and, optionally, when $R^6$ is $C_{1-8}$alkoxy, $R^5$ and $R^6$ are each taken together with the atoms to which they are attached to form a 6-membered monocyclic ring.

Examples of the present invention include compounds of Formula (I) wherein $R^5$ is hydrogen or $C_{1-6}$alkyl.

Examples of the present invention include compounds of Formula (I) wherein $R^5$ is hydrogen or methyl.

Embodiments of the present invention include compounds of Formula (I)
wherein $R^6$ is selected from the group consisting of $C_{1-8}$alkyl, $C_{1-8}$alkoxy, $C_{2-8}$alkenyl, heteroaryl, aryl and hydroxy,
wherein $C_{1-8}$alkyl, $C_{1-8}$alkoxy and $C_{2-8}$alkenyl are each optionally substituted on a terminal carbon atom with a substituent independently selected from the group consisting of $C_{1-4}$alkoxy, aryl, heteroaryl, heterocyclyl, $C_{1-6}$alkylcarbonyloxy-, $C_{1-6}$alkylcarbonylthio-, $C_{1-6}$alkoxycarbonyloxy-, ($C_{1-6}$)alkylaminocarbonyl-, di($C_{1-6}$)alkylaminocarbonyl- and hydroxy, and wherein heteroaryl and aryl are optionally substituted with one, two or three substituents independently selected from the group consisting of aryl, hydroxy, $C_{1-6}$alkoxy and halogen.

Embodiments of the present invention include compounds of Formula (I)

wherein $R^6$ is selected from the group consisting of $C_{1-6}$alkyl, $C_{1-6}$alkoxy, heteroaryl, aryl and hydroxy, wherein $C_{1-6}$alkyl is optionally substituted on a terminal carbon atom with a substituent selected from $C_{1-3}$alkoxy, aryl, or hydroxy; and wherein $C_{1-6}$alkoxy is optionally substituted on a terminal carbon with a substituent independently selected from the group consisting of $C_{1-6}$alkylcarbonyloxy- and di($C_{1-6}$)alkylaminocarbonyl-, and wherein heteroaryl and aryl are optionally substituted with one, two or three substituents independently selected from the group consisting of aryl, hydroxy, $C_{1-6}$alkoxy and halogen.

Examples of the present invention include compounds of Formula (I) wherein $R^6$ is selected from the group consisting of $C_{1-6}$alkyl and hydroxy.

Embodiments of the present invention include compounds of Formula (I) wherein $R^6$ is selected from the group consisting of methyl, ethyl, methoxypropyl, phenethyl, benzo[1,3]dioxol-5-yl-propyl, hydroxy and $C_{1-3}$alkoxy optionally substituted on $C_{1-3}$alkoxy with $C_{1-6}$alkylcarbonyloxy- and di($C_{1-6}$)alkylaminocarbonyl-.

Examples of the present invention include compounds of Formula (I) wherein $R^6$ is selected from the group consisting of methyl and hydroxy.

Embodiments of the present invention include compounds of Formula (I)

wherein $R^4$ is one, two or three substituents selected from the group consisting of hydrogen, $C_{1-6}$alkyl, $C_{2-6}$alkenyl, $C_{1-6}$alkoxy, aryl($C_{2-6}$)alkenyl, halogen, hydroxy, —C(=O)Cy, —C(=O)NR$^{31}$R$^{32}$, aryl, —CO$_2$H, oxo and cyano, wherein $C_{1-6}$alkyl and $C_{1-6}$alkoxy are optionally substituted on a terminal carbon atom with a substituent selected from aryl, —NR$^{33}$R$^{34}$, one, two or three halogen atoms, or hydroxy, and wherein aryl is optionally substituted with one, two or three substituents independently selected from the group consisting of hydrogen, $C_{1-6}$alkyl, $C_{1-6}$alkoxy, $C_{2-6}$alkenyl, —NH$_2$, —NH($C_{1-6}$)alkyl, —N($C_{1-6}$)dialkyl, aryl, heteroaryl, aryloxy, heteroaryloxy, halogen, hydroxy and nitro.

Embodiments of the present invention include compounds of Formula (I)

wherein $R^4$ is one, two or three substituents selected from the group consisting of hydrogen, $C_{1-6}$alkyl, $C_{2-6}$alkenyl, $C_{1-6}$alkoxy, aryl($C_{2-6}$)alkenyl, halogen, hydroxy, —C(=O)Cy, —C(=O)NR$^{31}$R$^{32}$, aryl, —CO$_2$H, oxo and cyano, wherein $C_{1-6}$alkyl and $C_{1-6}$alkoxy are optionally substituted with a substituent independently selected from —NR$^{33}$R$^{34}$, aryl, one, two or three halogen atoms, or hydroxy, and wherein aryl is optionally substituted with a substituent independently selected from the group consisting of hydrogen, $C_{1-6}$alkyl, $C_{1-6}$alkoxy, aryl, halogen, hydroxy and nitro.

Embodiments of the present invention include compounds of Formula (I)

wherein $R^4$ is one, two or three substituents selected from the group consisting of hydrogen, $C_{1-6}$alkyl, $C_{2-6}$alkenyl, $C_{1-6}$alkoxy, aryl($C_{2-6}$)alkenyl, halogen, hydroxy and —C(=O)Cy, wherein aryl is optionally substituted with a substituent selected from halogen and $C_{1-4}$alkoxy.

Examples of the present invention include compounds of Formula (I) wherein $R^4$ is one, two or three substituents selected from the group consisting of hydrogen, $C_{1-6}$alkyl, $C_{1-6}$alkoxy, halogen and hydroxy.

Embodiments of the present invention include compounds wherein $R^4$ is one or two or three substituents selected from the group consisting of hydrogen, fluorine, chlorine, bromine, hydroxy, methyl and methoxy.

Examples of the present invention include compounds of Formula (I) wherein $R^4$ is one or two or three substituents selected from the group consisting of hydrogen, chlorine, bromine, hydroxy, methyl and methoxy.

The present invention is further directed to a compound of Formula (Ia):

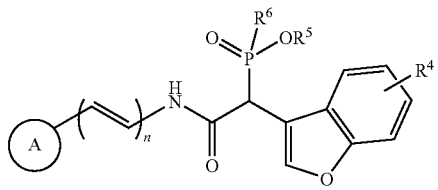

wherein

Ring A is aryl;

n is 0 or 1;

$R^5$ is selected from the group consisting of hydrogen and $C_{1-6}$alkyl;

$R^6$ is selected from the group consisting of $C_{1-8}$alkyl and hydroxy;

$R^4$ is one, two or three substituents selected from the group consisting of hydrogen, $C_{1-6}$alkyl, $C_{1-6}$alkoxy, halogen and hydroxy;

and enantiomers, diastereomers, polymorphs or pharmaceutically acceptable salts thereof.

Examples of the present invention include compounds of Formula (Ia) wherein Ring A is naphthyl and n is 0.

Examples of the present invention include compounds of Formula (Ia) wherein $R^5$ is hydrogen or methyl.

Examples of the present invention include compounds of Formula (Ia) wherein $R^6$ is selected from the group consisting of methyl and hydroxy.

Examples of the present invention include compounds of Formula (Ia) wherein $R^4$ is one or two or three substituents selected from the group consisting of hydrogen, chlorine, bromine, hydroxy, methyl and methoxy.

Embodiments of the phosphonic and phosphinic acids of the present invention include those compounds of Formula (Ia) wherein the $R^5$ and $R^6$ substituents are as previously defined for Formula (I) (which further include substitutions in any combination).

Embodiments of the present invention include a compound or an enantiomer, diastereomer, polymorph or pharmaceutically acceptable salt thereof selected from:

Cpd 1
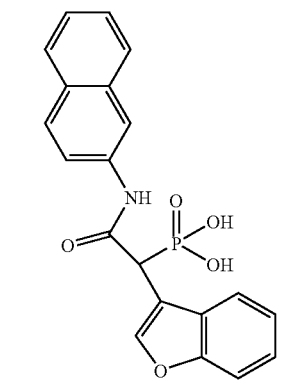
Cpd 2
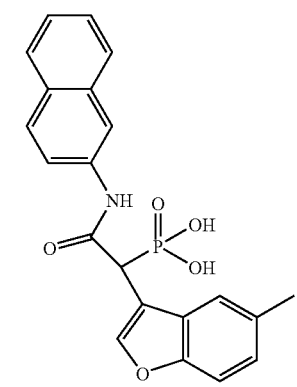
Cpd 3
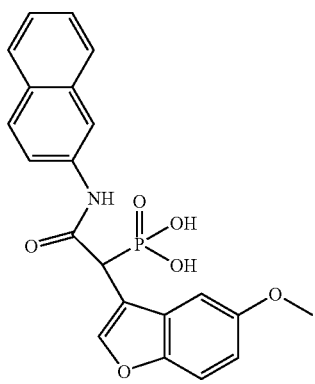
Cpd 4
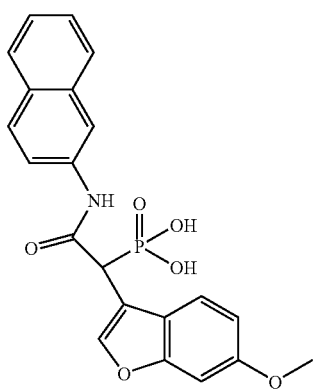
-continued
Cpd 5
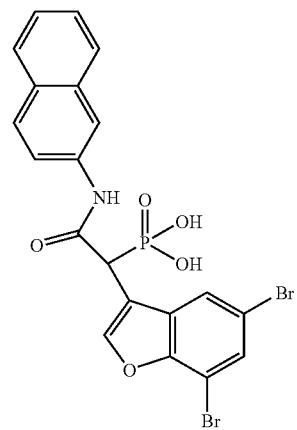
Cpd 6
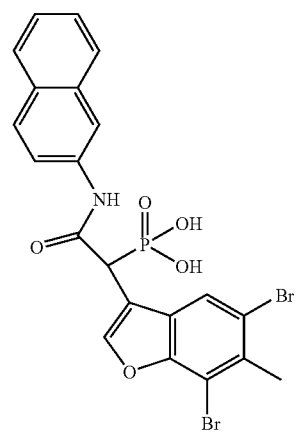
Cpd 7
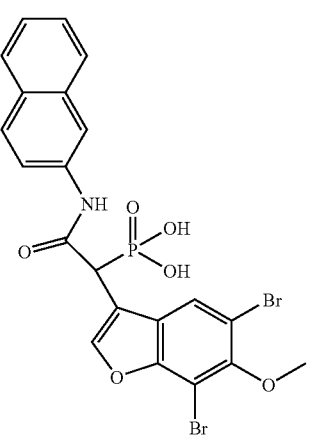
Cpd 8
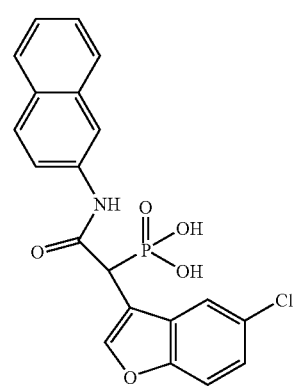

Cpd 9
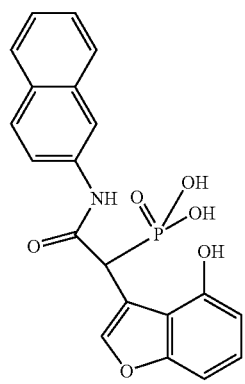
Cpd 13
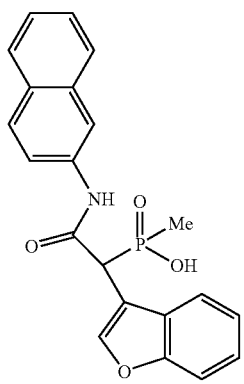
Cpd 10
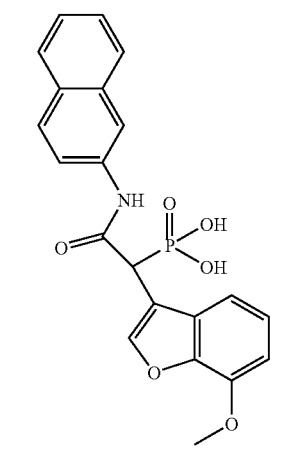
Cpd 14
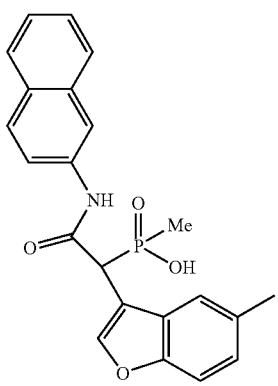
Cpd 11
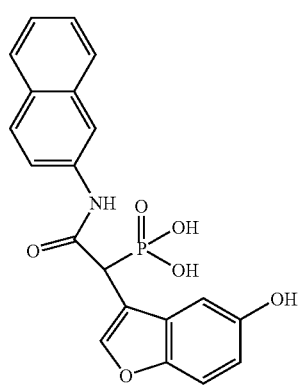
Cpd 15
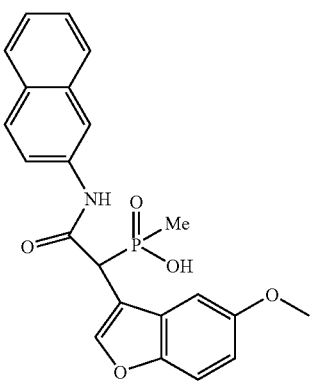
Cpd 12
Cpd 16
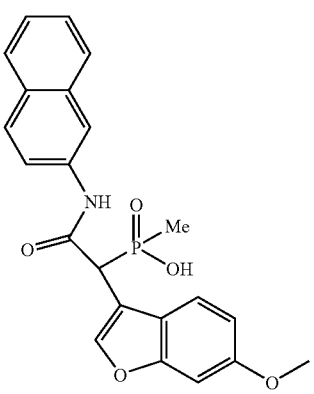

-continued
Cpd 17
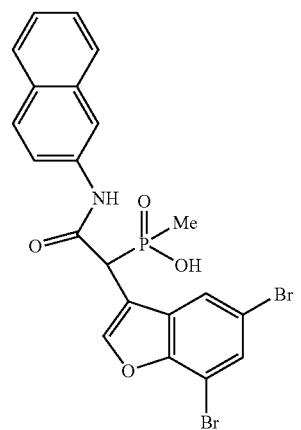
Cpd 18
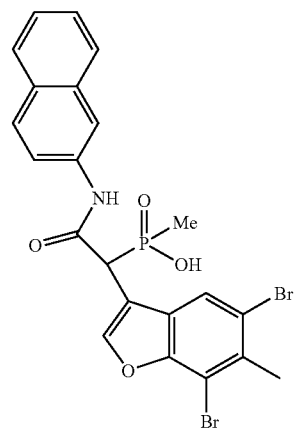
Cpd 19
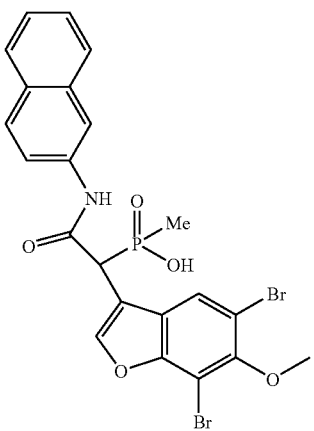
Cpd 20
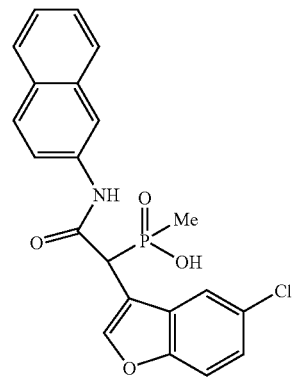
Cpd 21
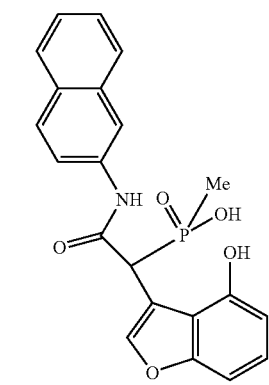
Cpd 22
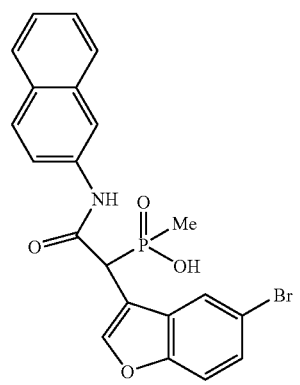
Cpd 23
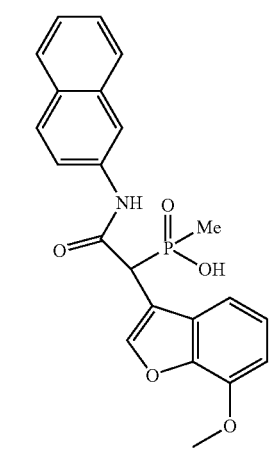
Cpd 24
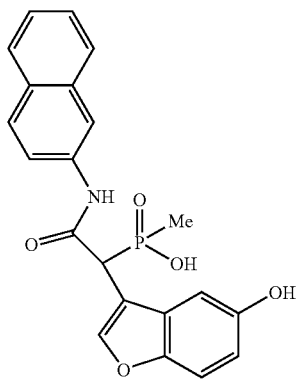

A representative compound of Formula (I) or an enantiomer, diastereomer, polymorph or pharmaceutically acceptable salt thereof includes a compound selected from the group consisting of:

| Cpd | Name |
|---|---|
| 1 | [benzofuran-3-yl-(naphthalen-2-ylcarbamoyl)-methyl]-phosphonic acid, |
| 2 | [(5-methyl-benzofuran-3-yl)-(naphthalen-2-ylcarbamoyl)-methyl]-phosphonic acid, |
| 3 | [(5-methoxy-benzofuran-3-yl)-(naphthalen-2-ylcarbamoyl)-methyl]-phosphonic acid, |
| 4 | [(6-methoxy-benzofuran-3-yl)-(naphthalen-2-ylcarbamoyl)-methyl]-phosphonic acid, |
| 5 | [(5,7-dibromo-benzofuran-3-yl)-(naphthalen-2-ylcarbamoyl)-methyl]-phosphonic acid, |
| 6 | [(5,7-dibromo-6-methyl-benzofuran-3-yl)-(naphthalen-2-ylcarbamoyl)-methyl]-phosphonic acid, |
| 7 | [(5,7-dibromo-6-methoxy-benzofuran-3-yl)-(naphthalen-2-ylcarbamoyl)-methyl]-phosphonic acid, |
| 8 | [(5-chloro-benzofuran-3-yl)-(naphthalen-2-ylcarbamoyl)-methyl]-phosphonic acid, |
| 9 | [(4-hydroxy-benzofuran-3-yl)-(naphthalen-2-ylcarbamoyl)-methyl]-phosphonic acid, |
| 10 | [(5-bromo-benzofuran-3-yl)-(naphthalen-2-ylcarbamoyl)-methyl]-phosphonic acid, |
| 11 | [(7-methoxy-benzofuran-3-yl)-(naphthalen-2-ylcarbamoyl)-methyl]-phosphonic acid, |
| 12 | [(5-hydroxy-benzofuran-3-yl)-(naphthalen-2-ylcarbamoyl)-methyl]-phosphonic acid, |
| 13 | [benzofuran-3-yl-(naphthalen-2-ylcarbamoyl)-methyl]-methyl-phosphinic acid, |
| 14 | methyl-[(5-methyl-benzofuran-3-yl)-(naphthalen-2-ylcarbamoyl)-methyl]-phosphinic acid, |
| 15 | [(5-methoxy-benzofuran-3-yl)-(naphthalen-2-ylcarbamoyl)-methyl]-methyl-phosphinic acid, |
| 16 | [(6-methoxy-benzofuran-3-yl)-(naphthalen-2-ylcarbamoyl)-methyl]-methyl-phosphinic acid, |
| 17 | [(5,7-dibromo-benzofuran-3-yl)-(naphthalen-2-ylcarbamoyl)-methyl]-methyl-phosphinic acid, |
| 18 | [(5,7-dibromo-6-methyl-benzofuran-3-yl)-(naphthalen-2-ylcarbamoyl)-methyl]-methyl-phosphinic acid, |
| 19 | [(5,7-dibromo-6-methoxy-benzofuran-3-yl)-(naphthalen-2-ylcarbamoyl)-methyl]-methyl-phosphinic acid, |
| 20 | [(5-chloro-benzofuran-3-yl)-(naphthalen-2-ylcarbamoyl)-methyl]-methyl-phosphinic acid, |
| 21 | [(4-hydroxy-benzofuran-3-yl)-(naphthalen-2-ylcarbamoyl)-methyl]-methyl-phosphinic acid, |
| 22 | [(5-bromo-benzofuran-3-yl)-(naphthalen-2-ylcarbamoyl)-methyl]-methyl-phosphinic acid, |
| 23 | [(7-methoxy-benzofuran-3-yl)-(naphthalen-2-ylcarbamoyl)-methyl]-methyl-phosphinic acid, and |
| 24 | [(5-hydroxy-benzofuran-3-yl)-(naphthalen-2-ylcarbamoyl)-methyl]-methyl-phosphinic acid. |

Compound Forms

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

The present invention includes within its scope prodrugs of the compounds of this invention. In general, such prodrugs will be functional derivatives of the compounds, which are readily convertible in vivo into an active compound.

Thus, in the methods of treatment of the present invention, the term "administering" shall encompass the treatment of the various disorders described with the compound specifically disclosed or a prodrug compound which would be obviously included within the scope of the invention although not specifically disclosed. Conventional procedures for the selection and preparation of suitable prodrug derivatives are described, for example, in "*Design of Prodrugs*", ed. H. Bundgaard, Elsevier, 1985. Phosphonic acid prodrugs (as described in De Lombaert S., et al, Non-Peptidic Inhibitors of Neutral Endopeptidase 24.11; Design and Pharmacology of Orally Active Phosphonate Prodrugs, *Bioorganic and Medicinal Chemistry Letters,* 1995, 5(2), 151-154; and, De Lombaert S., et al, N-Phosphonomethyl Dipeptides and Their Phosphonate Prodrugs, a New Generation Neutral Endopeptidase (NEP, EC 3.424.11) Inhibitors, *J. Med. Chem.,* 1994, 37, 498-511) and phosphinic acid prodrugs are intended to be included within the scope of the present invention.

The compounds according to this invention may have at least one chiral center and thus may exist as enantiomers. In addition, the compounds of the present invention may also possess two or more chiral centers and thus may also exist as diastereomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active base, followed by fractional crystallization and regeneration of the compounds of this invention. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents and as such are also intended to be encompassed within the scope of this invention.

Chemical Definitions

As used herein, unless otherwise noted, "alkyl" whether used alone or as part of a substituent group refers to straight and branched carbon chains having 1 to 8 carbon atoms or any number within this range. Examples include methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl and the like.

The term "alkoxy" refers to an —O-alkyl substituent group, wherein alkyl is as defined supra. Examples include methoxy, ethoxy, propoxy and the like.

The term "alkylthio" refers to an —S-alkyl substituent group, wherein the alkyl portion may be further substituted where allowed by available valences.

The terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. Examples for alkenyl include ethenyl (also referred to as vinyl), iso-propenyl, allyl (also referred to as propenyl), propylidene and the like. Examples for alkynyl include ethynyl, propynyl and the like. Alkenyl and alkynyl radicals may be attached to a core molecule and further substituted on any atom when allowed by available valences.

An alkyl and alkoxy chain may be substituted on a terminal carbon atom or, when acting as a linking group, within the carbon chain where allowed by available valences.

The term "alkylthio" refers to a —S-alkyl substituent group, wherein the alkyl portion may be further substituted where allowed by available valences.

The term "$C_{1-6}$alkylcarbonyloxy" refers to a —O—C(O)—$C_{1-6}$alkyl substituent group, wherein the alkyl portion may be further substituted where allowed by available valences.

The term "alkoxycarbonyl" refers to a —C(O)—O—$C_{1-6}$alkyl substituent group, wherein the alkyl portion may be further substituted where allowed by available valences.

The term "$C_{1-6}$alkoxycarbonyloxy" refers to a —O—C(O)—O—$C_{1-6}$alkyl substituent group, wherein the alkyl portion may be further substituted where allowed by available valences.

The term "$C_{1-6}$alkylcarbonylthio" refers to a —S—C(O)—$C_{1-6}$alkyl substituent group, wherein the alkyl portion may be further substituted where allowed by available valences.

The term "$(C_{1-6})$alkylaminocarbonyl" refers to a —C(O)—NH—$C_{1-6}$alkyl or —C(O)—NH($C_{1-6}$)alkyl substituent group, wherein the amino or alkyl portion may be further substituted where allowed by available valences.

The term "di$(C_{1-6})$alkylaminocarbonyl" refers to a —C(O)—N($C_{1-6}$alkyl)$_2$ or —C(O)—N($C_{1-6}$)dialkyl substituent group, wherein the alkyl portion may be further substituted where allowed by available valences.

The term "cycloalkyl" refers to saturated or partially unsaturated, moncyclic or polycyclic hydrocarbon rings of from 3 to 20 carbon atom members (preferably from 3 to 14 carbon atom members). Further, a cycloalkyl ring may optionally be fused to one or more cycloalkyl rings. Examples of such rings include, and are not limited to, cyclopropyl, cyclobutyl, cyclopentyl, cyclohexyl, cycloheptyl, and adamantanyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. Alternatively, the heterocyclyl ring may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety (spiro-fused). For instant compounds of the invention, the carbon atom ring members that form the heterocyclyl ring are fully saturated. Other compounds of the invention may have a partially saturated heterocyclyl ring.

Additionally, the heterocyclyl can be bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl, and piperazinyl.

The term "heterocyclylcarbonyl" refers to a —C(O)-heterocyclyl substituent group, wherein the heterocyclyl portion may be further substituted where allowed by available valences.

The term "aryl" refers to an unsaturated, aromatic monocyclic ring of 6 carbon members or to an unsaturated, aromatic polycyclic ring of from 10 to 20 carbon members. Examples of such aryl rings include, and are not limited to, phenyl, naphthalenyl and anthracenyl.

The term "benzo fused cycloalkyl" refers to a bicyclic or tricyclic ring structure wherein at least one of the ring substituents is phenyl or naphthalenyl and at least one of the other substituents is a cycloalkyl ring (as cycloalkyl was previously defined). For the purpose of these definitions, the cycloalkyl rings may be fused to an additional benzene ring (to provide fused multiple ring systems such as fluorene). Example of such benzo fused cycloalkyls include, but are not limited to, indanyl, 1,2,3,4-tetrahydronaphthalenyl and fluorenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one, two or three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, and quinazolinyl.

The term "aryl($C_{1-6}$)alkyl" means an $C_{1-6}$alkyl group substituted with an aryl group (e.g., benzyl and phenethyl), as in the formula —$C_{1-6}$alkyl-aryl, wherein aryl may be substituted on any alkyl chain carbon atom where allowed by available valences.

The term "aryl($C_{2-6}$)alkenyl" means an $C_{2-6}$alkenyl group substituted with an aryl group, as in the formula —$C_{2-6}$alkenyl-aryl, wherein aryl may be substituted on any alkenyl chain carbon atom where allowed by available valences.

The term "arylalkoxy" indicates an alkoxy group substituted with an aryl group (e.g., benzyloxy), as in the formula —O-alkyl-aryl, wherein aryl may be substituted on any alkyl chain carbon atom where allowed by available valences.

The term "aryloxy" indicates an oxy group substituted with an aryl group (e.g., benzoxy), as in the formula —O-aryl.

The term "heteroaryloxy" indicates an alkoxy group substituted with a heteroaryl group, as in the formula —O-alkyl-heteroaryl, wherein heteroaryl may be substituted on any alkyl chain carbon atom where allowed by available valences.

The term "halogen" refers to fluorine, chlorine, bromine, and iodine. Substituents that are substituted with multiple halogen atoms are substituted in a manner that provides compounds which are stable (e.g. —$CF_3$ or —$OCF_3$).

Whenever the term "alkyl" or "aryl" or either of their prefix roots appear in a name of a substituent (e.g., arylalkyl and alkylamino), it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified.

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

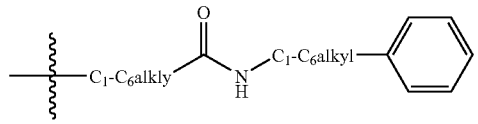

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Pharmaceutical Compositions and Methods of Use

Illustrative of the invention is a composition comprising a pharmaceutically acceptable carrier and any of the compounds described above. Also illustrative of the invention is a composition made by mixing any of the compounds described above and a pharmaceutically acceptable carrier. A further illustration of the invention is a process for making a composition comprising mixing any of the compounds described above and a pharmaceutically acceptable carrier. The present invention also provides compositions comprising one or more compounds of this invention in association with a pharmaceutically acceptable carrier.

The compounds of the present invention are useful serine protease inhibitors (in particular, inhibitors of chymase) useful for treating inflammatory or serine protease mediated disorders. Serine proteases such as chymase produced by mast cells have been recognized to be involved in a variety of inflammatory and wound healing events (e.g., angiogenesis, collagen deposition and cell proliferation). Chymase plays these roles by activating a variety of pre-existing factors present in the microenvironment surrounding the mast cells. For example, chymase activates SCF, angiotensin I to angiotensin II, endothelin 1, type 1 procollagen, metalloprotienases, IL-1B, TGF-β, as well as, degrades the extracellular matrix (de Paulis et al. Int Arch Allerg Immunol 118 (1999)

422-425; Longley et al. Proc Natl Acad Sci USA 94 (1997) 9017-9021). Consequently, the release of chymase plays significant role in a variety of pathological conditions associated with vascular proliferation, fibrosis, tissue remodeling, inflammation, and the like.

Some of these, inflammatory or serine protease mediated disorders include, and are not limited to, allergic rhinitis, viral rhinitis, asthma, chronic obstructive pulmonary diseases, bronchitis, pulmonary emphysema, acute lung injury (e.g. adult (acute) respiratory distress syndrome), psoriasis, arthritis, reperfusion injury, ischemia, hypertension, hypercardia myocardial infarction, heart failure damage associated with myocardial infarction and cardiac hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars rheumatoid arthritis, bullous pemphigoid and atherosclerosis.

Additionally, these compounds can be used for modulating wound healing and remodeling (e.g., cardiac hypertrophy) as well as immune modulation. The utility of the compounds to treat inflammatory or serine protease mediated disorders is illustrated by the following non-limiting discussions of the proposed mechanisms of actions of chymase. Other disorders that can be treated with chymase inhibitors can be determined according to the procedures described herein and the use of animal knock-out models and the like.

As mentioned above, chymase converts angiotensin I into angiotensin II, and this activity has been associated with vascular proliferation. In human vascular extracts only about 8% of angiotensin II activity is inhibited with an angiotensin converting enzyme inhibitor (lisinopril) while 95% is inhibited by a chymase inhibitor. In vein grafts, vascular injury associated with catheter or balloon injury, chymase induces vascular hyperplasia and restenosis in dogs (Takai and Miyazaki, 21 (2003) 185-189). This same mechanism of action would also be expected to apply to restenosis associated with the use of vascular stents. Pathological serine protease mediated disorders associated with angiotensin II, including but not limited to hypertension, hypercardia myocardial infarction, arteriosclerosis, saroidosis, vascular stenosis or restenosis (e.g., associated with vascular injury, angioplasty, vascular stents or vascular grafts), and the like.

Pathological fibrosis can be associated with the degeneration of organs (e.g., skin, heart, kidneys or liver) or as an undesirable outcome of surgery. Preventing the formation of pathological fibrosis would be beneficial in a variety of diseases. For example, mast cell chymase has been implicated in pulmonary fibrosis, kidney fibrosis, liver fibrosis, post surgical adhesion formation, systemic sclerosis, keloid scars, and the like.

In the heart, mast cells have been implicated in cardiac hypertrophy, which involves both fibrosis and remodeling. Cardiac hypertrophy develops to preserve its function by normalizing chamber wall stress. Mast cells have been implicated as being involved in the development of myocardial fibrosis and systolic pressure over load induced hypertrophy (Hara et al., J. Exp. Med. 195 (2002) 375-381). The remodeling of the heart associated under these conditions is believed to involve mast cell chymase, which activates endothelin 1, matrix metalloproteinases and TGF-β. Chymase inhibitors have been shown to exert favorable cardioprotective action in a dog model of hypertrophy (Matsumoto et al., Circulation 107 (2003) 2555-2558).

In the kidneys, mast cell chymase has also been implicated in pathological fibrosis. For example, glomerulonephritis has also been reported to involve mast cells (Ehara and Shigematsu, Kidney Inter. 54 (1998) 1675-1683). The results of this found that mast cells were one of the constitutive cell types in the interstitium of IgA nephritis patients and contributed to interstitial fibrosis resulting in deterioration of renal function. Similarly, liver fibrosis has been associated with mast cells (Yamashiro et al., Virchows Arch. 433 (1998) 471-479). Although, the mechanisms for fibrosis in the kidney and liver have not been as well defined as for coronary fibrosis, it is very likely that chymase is operating through similar signaling pathways to cause fibrosis (especially in liver fibrosis where fibrosis seem to be occurring more frequently where mast cells stained positive for chymase).

Chymase is also involved in the formation of fibrous adhesions associated with surgery. Chymase inhibitors have been tested in two different animals models and found to reduce the number of adhesions (Okamoto et al., J. Surg. Res. 107 (2002) 219-222 and Lucas et al., J. Surg. Res. 65 (1999) 135). It has been suggested that the prevention of adhesions is associated with blocking the activation of latent TGF-β by chymase (Yoa et al., J. Surg. Res. 92 (2000) 40-44).

Collagen induced arthritic mice show increased numbers of mast cells and expression of chymase in fibroproliferative inflammation (Kakizoe et al., Inflamm. Res. 48 (1999) 318-324). In human rheumatoid arthritis increased mast cell density in the superficial synovium is associated with the severity of the disease (Grotis-Graham and McNeil, Arthritis & Rheumatism 40 (1997) 479-489). It was theorized by these authors that chymase and its ability to activate metalloproteinases plays a significant role in the rapid functional deterioration observed in rheumatoid arthritis.

Mast cell chymase has been implicated in atherosclerosis via its ability to cleave apolipoprotein B-100 of LDL which facilitates lipoprotein aggregation and uptake by macrophages (Paananen et al., J. Biol. Chem. 269 (1994) 2023-2031). Chymase also degrades apolipoprotein A of HDL, which would reduce cholesterol efflux and increases lipid deposition (Lindstedt et al., J. Clin. Invest. 97 (1996) 2174-2182). Thus, chymase is involved in two different pathways to atherosclerosis.

An embodiment of the invention is a method for treating inflammatory or serine protease mediated disorders in a subject in need thereof which comprises administering to the subject a therapeutically effective amount of any of the compounds or compositions described above.

An example of the invention is a method for treating an inflammatory or chymase mediated disorder selected from the group consisting of allergic rhinitis, viral rhinitis, asthma, chronic obstructive pulmonary diseases, bronchitis, pulmonary emphysema, psoriasis, arthritis, reperfusion injury, ischemia, hypertension, hypercardia myocardial infarction, heart failure damage associated with myocardial infarction and cardiac hypertrophy, arteriosclerosis, sarcoidosis, vascular stenosis or restenosis, pulmonary fibrosis, kidney fibrosis, liver fibrosis, post surgical adhesion formation, systemic sclerosis, keloid scars, rheumatoid arthritis, bullous pemphiguoid and atherosclerosis in a subject in need thereof comprising administering to the subject a therapeutically effective amount of any of the compounds of Formula (I) or Formula (Ia) or compositions thereof as described above.

An example of the invention is a use of a compound of Formula (I) or Formula (Ia) for the preparation of a medicament for treating an inflammatory or serine protease mediated disorder in a subject in need thereof.

An embodiment of a serine protease inhibited according to the use of a compound in a medicament is chymase.

An example of the use of a compound in a medicament for treating inflammatory or chymase mediated disorders is a disorder selected from the group consisting of allergic rhinitis, viral rhinitis, asthma, chronic obstructive pulmonary diseases, bronchitis, pulmonary emphysema, psoriasis, arthritis, reperfusion injury, ischemia, hypertension, hypercardia myocardial infarction, heart failure damage associated with myocardial infarction and cardiac hypertrophy, arteriosclerosis, sarcoidosis, vascular stenosis or restenosis, pulmonary fibrosis, kidney fibrosis, liver fibrosis, post surgical adhesion formation, systemic sclerosis, keloid scars, rheumatoid arthritis, bullous pemphiguoid and atherosclerosis.

An example of the use of a compound in a medicament for treating an inflammatory or serine protease mediated disorder is a disorder selected from the group consisting of allergic rhinitis, asthma, chronic obstructive pulmonary disease, bronchitis, pulmonary emphysema, acute lung injury, heart failure damage associated with myocardial infarction and cardiac hypertrophy.

An example of the use of a compound in a medicament for treating an inflammatory or serine protease mediated disorder is a disorder selected from the group consisting of allergic rhinitis, asthma and heart failure damage associated with myocardial infarction and cardiac hypertrophy.

The term "treating" as used herein refers to a method for improving, halting, retarding or palliating an inflammatory or serine protease mediated disorder in the subject in need thereof. All such methods of treatment are intended to be within the scope of the present invention.

In accordance with the methods of the present invention, the individual components of the compositions described herein can also be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal (preferably, a mammal; most preferably, a human), having been the object of treatment, observation, or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare the compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating compositions have been described in numerous publications such as *Pharmaceutical Dosage Forms: Tablets, Second Edition. Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a composition of the present invention in liquid dosage form for oral, topical, inhalation/insufflation and parenteral administration, any of the usual pharmaceutical media or excipients may be employed. Thus, for liquid dosage forms, such as suspensions (i.e., colloids, emulsions and dispersions) and solutions, suitable carriers and additives include but are not limited to pharmaceutically acceptable wetting agents, dispersants, flocculation agents, thickeners, pH control agents (i.e., buffers), osmotic agents, coloring agents, flavors, fragrances, preservatives (i.e., to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents, and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions such as tablets, the principal active ingredient is mixed with a pharmaceutical carrier, e.g., conventional tabletting ingredients such as diluents, binders, adhesives, disintegrants, lubricants, antiadherents, and glidants.

Suitable diluents include, but are not limited to, starch (i.e., corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose, dicalcium phosphate, calcium sulfate dihydrate, calcium lactate trihydrate, and the like.

Suitable binders and adhesives include, but are not limited to accacia gum, guar gum, tragacanth gum, sucrose, gelatin, glucose, starch, and cellulosics (i.e. methylcellulose, sodium carboxymethyl-cellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose, polyethylene glycol, polysaccharide acids, bentonites, polyvinylpyrrolidone, polymethacrylates and pregelatinized starch), and the like.

Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e., corn starch, etc.), gums (i.e., agar, guar, locust bean, karaya, pectin, and tragacanth gum), cross-linked polyvinylpyrrolidone, and the like.

Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate, and the like. Suitable glidants include, but are not limited to, talc, cornstarch, silica, and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation, and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention.

The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate, cellulose acetate phthalate, polyvinyl acetate phthalate, hydroxypropyl methylcellulose phthalate, hydroxy-propyl methylcellulose acetate succinate, methacrylate and ethylacrylate copolymers, and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e., beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

Suitable suspending agents for aqueous suspensions, include synthetic and natural gums such as, acacia, agar, alginate (i.e., propylene alginate, sodium alginate, and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e., carboxypolymethylene), and polyethylene glycol; clays such as bentonite, hectorite, attapulgite or sepiolite; and other pharmaceutically acceptable suspending agents such as lecithin, gelatin, or the like.

Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235, and combinations thereof. Suitable deflocculating or dispersing agent include pharmaceutical grade lecithins. Suitable flocculating agent include but are not limited to simple neutral electrolytes (i.e., sodium chloride, potassium, chloride, and the like), highly charged insoluble polymers and polyelectrolyte species, water soluble divalent or trivalent ions (i.e., calcium salts, alums or sulfates, citrates and phosphates (which can be used jointly in formulations as pH buffers and flocculating agents).

Suitable preservatives include but are not limited to parabens (i.e., methyl, ethyl, n-propyl and n-butyl), sorbic acid, thimerosal, quaternary ammonium salts, benzyl alcohol, benzoic acid, chlorhexidine gluconate, phenylethanol, and the like. There are many liquid vehicles that may be used in liquid pharmaceutical dosage forms, however, the liquid vehicle that is used in a particular dosage form must be compatible with the suspending agent(s).

For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers, and the like. Conversely, polar liquids such as water, alcohols, polyols and glycols are best used with suspending agents such as higher HLB surfactants, clays silicates, gums, water soluble cellulosics, water soluble polymers, and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in a form suitable for intranasal or inhalation therapy. For such therapy, compounds of the present invention are conveniently delivered in the form of a solution or suspension from a pump spray container that is squeezed or pumped or as an aerosol spray from a pressurized container or a nebulizer (such as, a metered dose inhaler, a dry powder inhaler or other conventional or non-conventional modes or devices for inhalation delivery) using a suitable propellant (such as, dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (such as, those made from gelatin) for use in an inhaler or insufflator may be formulated containing a powder mix of a compound of the invention and a suitable powder base such as lactose or starch.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines, and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, and polyethyleneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, poly-orthoesters, polyacetals, polydihydropyrans, polycyanoacrylates, and cross-linked or amphipathic block copolymers of hydrogels and blends thereof.

The therapeutically effective amount of a compound or composition thereof may be from about 0.001 mg/kg/dose to about 300 mg/kg/dose. Preferably, the therapeutically effective amount may be from about 0.001 mg/kg/dose to about 100 mg/kg/dose. More preferably, the therapeutically effective amount may be from about 0.001 mg/kg/dose to about 50 mg/kg/dose. Most preferably, the therapeutically effective amount may be from about 0.001 mg/kg/dose to about 30 mg/kg/dose. Therefore, the therapeutically effective amount of the active ingredient contained per dosage unit (e.g., tablet, capsule, powder, injection, suppository, teaspoonful, and the like) as described herein will be in the range of from about 1 mg/day to about 21,000 mg/day for a subject, for example, having an average weight of 70 kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Abbreviations used in the instant specification, particularly the Schemes and Examples, are as follows:

| Abbreviation | Meaning |
| --- | --- |
| Boc | tert-butoxycarbonyl |
| BOC-ON | 2-(tert-butoxycarbonyloxyimino)-2-phenylacetonitrile |
| BuLi | n-butyllithium |
| t-BuOH | tert-butanol |
| Cpd | compound |
| LiOH | lithium hydroxide |
| min/h/d | minutes/hour/hours/day/days |
| rt/RT | room temperature |
| TEA or Et$_3$N | triethylamine |
| THF | tetrahydrofuran |
| TFA | trifluoroacetic acid |
| TMSBr | bromotrimethylsilane |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds and stereoisomers, racemic mixtures, diasteromers and enantiomers thereof can be synthesized using the intermediates prepared in accordance to the general schemes and other materials, compounds and reagents known to those skilled in the art. All such compounds, stereoisomers, racemic mixtures, diasteromers and enantiomers thereof are intended to be encompassed within the scope of the present invention. Since the scheme is an illustration, the invention should not be construed as being limited by the chemical reactions and conditions expressed. The preparation of the various starting materials used in the scheme is well within the skill of persons versed in the art.

Scheme A

Scheme A illustrates the general method for the preparation of compounds representative of the present invention.

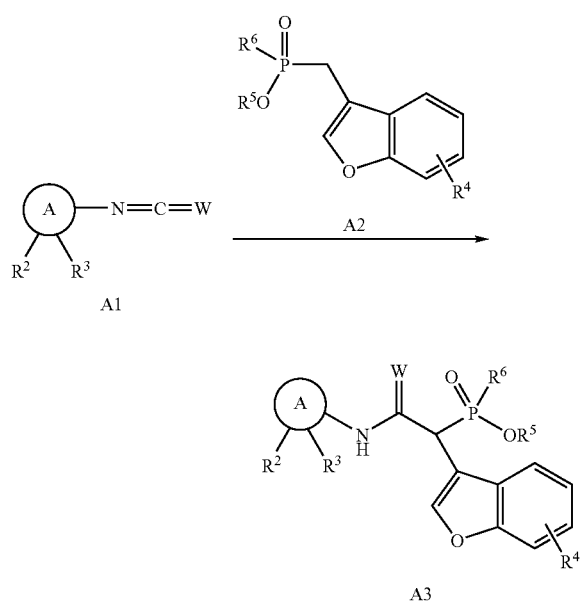

A phosphonate or phosphinate anion (prepared from its corresponding phosphonate or phosphinate Compound A2 and an organometallic base such as n-butyllithium) is reacted with an isocyanate Compound A1 in a solvent such as THF to afford an amidophosphonate or amidophosphinate compound A3. One versed in the art will recognize that conventional chemical transformations may be utilized to prepare certain $R^2$ and $R^3$ substituents of the present invention. For example, for the preparation of a compound wherein $R^3$ is amino, a nitro group may be reduced with hydrazine hydrate in the presence of a palladium catalyst; or, for the preparation of a compound wherein $R^3$ is ureido, a compound in which $R^3$ is an amino group may be reacted with a cyanate salt or the like.

Compound A2, wherein $R^5$ and $R^6$ are as previously defined, may be made according to known methods (Katritsky et. al. *Org. Prep. Proced. Int.*, 1990, 22(2), 209-213; *J. Am. Chem. Soc.*, 2002, 124, 9386-9387; and *Chem. Ber.*, 1963, 96, 3184-3194), may be prepared from a commercially available or known haloalkyl substituted heteroaryl ring.

Fluorinated $R^6$ compounds can be made following methods known in the art such as the methods similar those set forth in Garabadzhia et al., Journal General Chemistry USSR, English translation, 1981, pages 1905-1910.

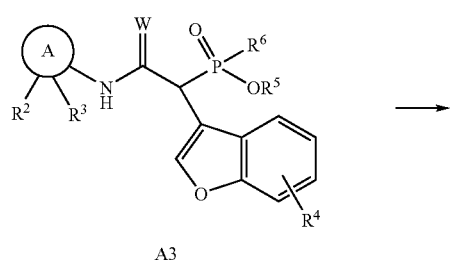

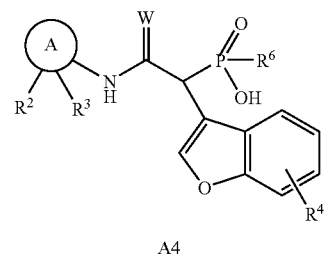

Compound A3 may be dealkylated with bromotrimethylsilane in a solvent such as pyridine, followed by treatment with dilute HCl to afford Compound A4.

Scheme B

Scheme B shows a method for preparing Compound B3 wherein $R^6$ is an alkyl or alkenyl substituent using methods described in the literature (*J. Organomet. Chem.* 2002, 643-644, 154-163; *J. Amer. Chem. Soc.* 2002, 124, 9386-9387).

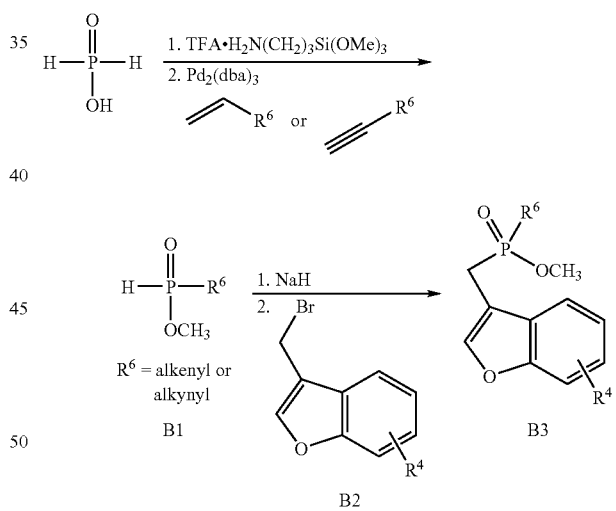

Compound B2 (wherein $R^4$ is other than hydrogen) is known; certain analogs of which may be commercially available and may be alternatively prepared according to *J. Med. Chem.* 1997, 40 (17) 2706-2725. Another method for preparing such compounds (wherein $R^4$ is other than hydrogen) is described in the literature (*Med. Chem.* 1995, 38(17), 3297-3312; *Bioorg. Med. Chem.* 1999, 7, 2697-2704).

Compound B2 (wherein $R^4$ is hydrogen) is prepared according to a procedure described in *J. Med. Chem.*, 1997, 40 (17) 2706-2725.

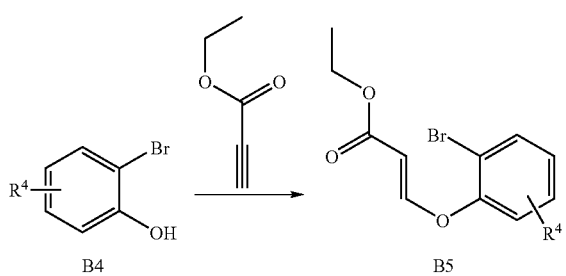

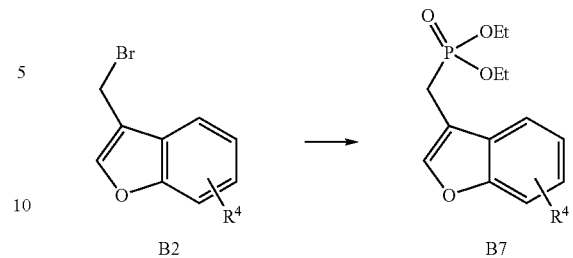

Compound B4 is reacted with a solution of ethyl propiolate (in the presence of a solvent such as TEA and THF) to provide a Compound B5.

Compound B2 is reacted with a triethylphosphite solution (in a solvent such as dry toluene) to provide a Compound B7 that is carried forward according to the procedure of Scheme A to provide compounds representative of the present invention.

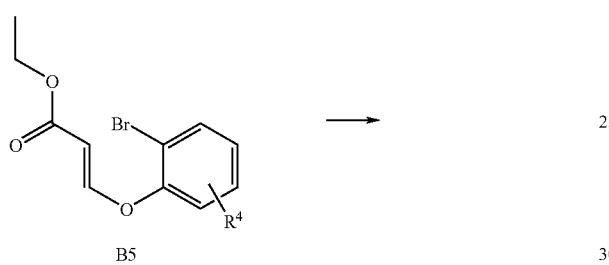

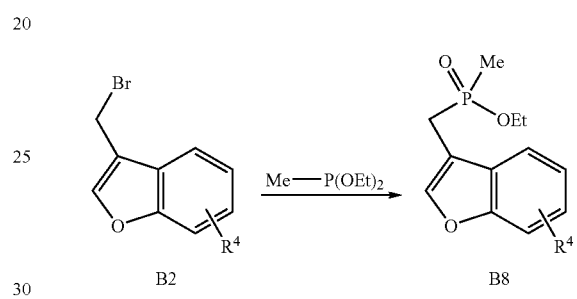

Compound B2 is reacted with a methyl-diethylphosphite solution (in a solvent such as dry toluene) to provide a Compound B8 that is carried forward according to the procedure of Scheme A to provide compounds representative of the present invention.

Scheme C

Scheme C illustrates a general method for the preparation of compounds representative of the present invention wherein Ring A of Formula (I) is an aryl substituent and n of Formula (I) is equal to 1.

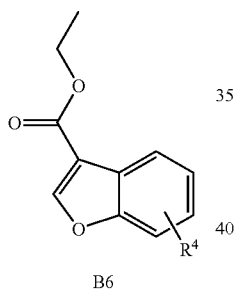

Compound B5 is reacted in the presence of a catalyst (such as $Pd(OAc)_2$ and $PPH_3$) and a basic solution (such as $NaHCO_3$ in DMF) to provide a Compound B6.

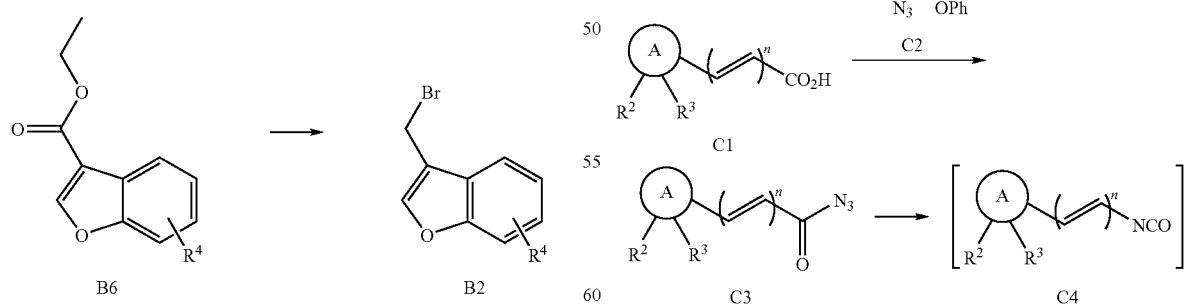

Compound B6 is reacted with a reagent solution (such as DIBAL-H in a solvent such as $CH_2Cl_2$) to provide a non-isolated intermediate which is then reacted in the presence of a catalyst solution (such as $PPh_3Br_2$ in a solvent such as $CCl_4$) to provide Compound B2.

Reaction of an α/β-unsaturated carboxylic acid, Compound C1, with phosphorazidic acid dialkyl ester Compound C2 provides Compound C3. Compound C3 may subsequently undergo a Curtius rearrangement to afford an isocyanate intermediate, Compound C4.

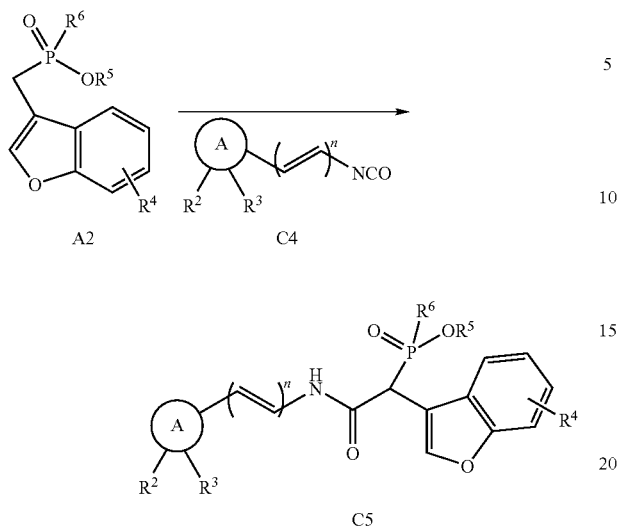

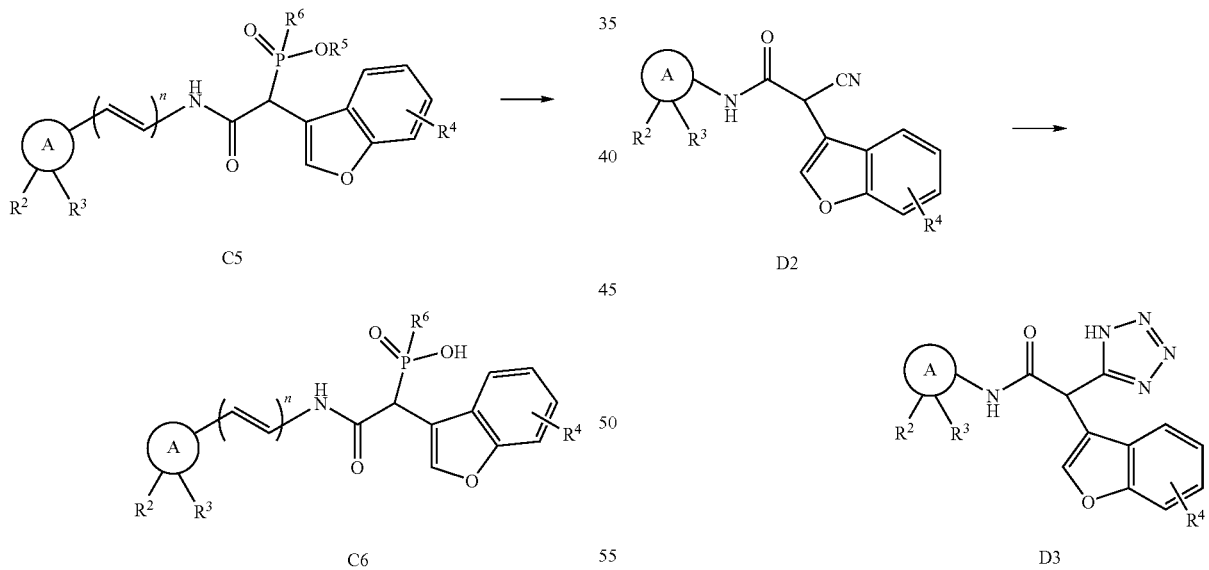

Compound C4 is reacted with a phosphonate or phosphinate anion (using Compound C2 from Scheme A or Compound B3 from Scheme B) in a mixture of an aprotic solvent such as THF and an organometallic base (such as n-butyllithium) to yield amidophosphonate or amidophosphinate Compound C5.

Compound D1 (where $R^4$ is hydrogen) is known and commercially available.

Compound D1 may be dissolved in an aprotic solvent, treated with an organometallic base such as n-BuLi, and subsequently reacted with isocyanate Compound A1 to afford Compound D2.

Compound C5 may be dealkylated with bromotrimethylsilane, followed by treatment with dilute HCl to afford Compound C6.

Compound D2 may undergo a cycloaddition reaction with sodium azide to provide Compound D3.

Scheme D

Scheme E

Scheme D further illustrates the preparation of compounds representative of the present invention wherein Y of Formula (I) is a heteroaryl substituent.

Scheme E shows the preparation of compounds representative of the present invention wherein Y of Formula (I) is a sulfonic acid.

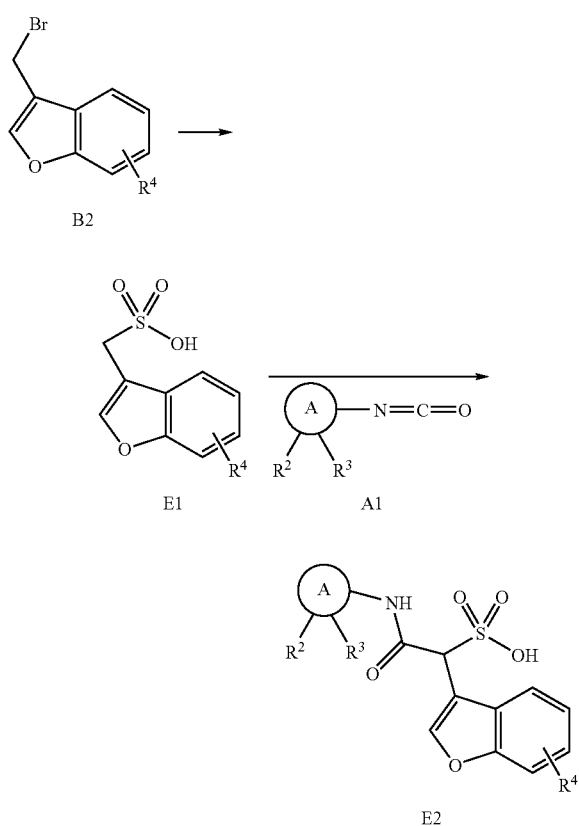

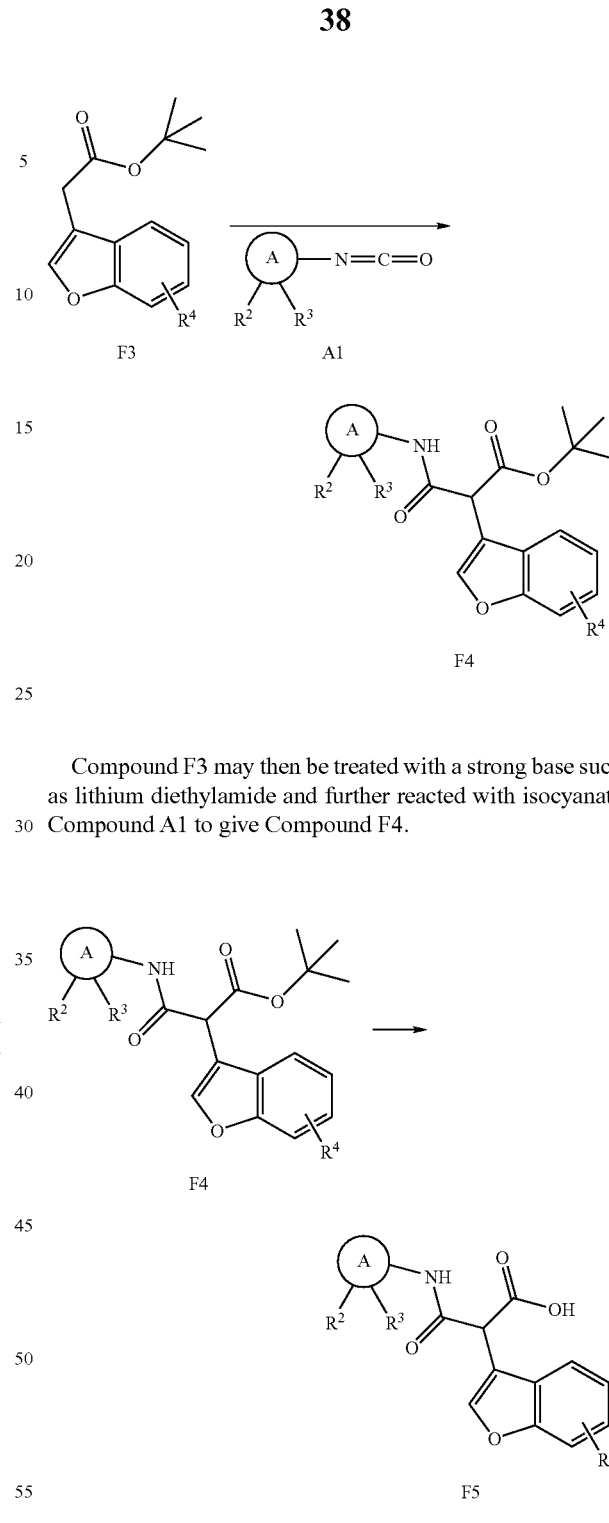

Compound B2 may be treated with sodium sulfite to afford Compound E1. Compound E1 may then be treated with an organometallic base such as isopropylmagnesium bromide and reacted with isocyanate Compound A1 to yield Compound E2.

Scheme F

Scheme F illustrates the preparation of compounds representative of the present invention wherein Y of Formula (I) is a carboxylic acid.

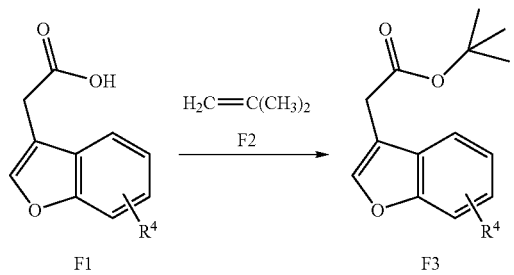

Compound F1 may be reacted with isobutylene under acidic conditions to provide ester Compound F3.

Compound F3 may then be treated with a strong base such as lithium diethylamide and further reacted with isocyanate Compound A1 to give Compound F4.

Compound F4 is converted into its corresponding carboxylic acid Compound F5 by treatment with TFA.

Scheme G

Scheme G illustrates the preparation of compounds representative of the present invention wherein Y of Formula (I) is hydroxymethyl.

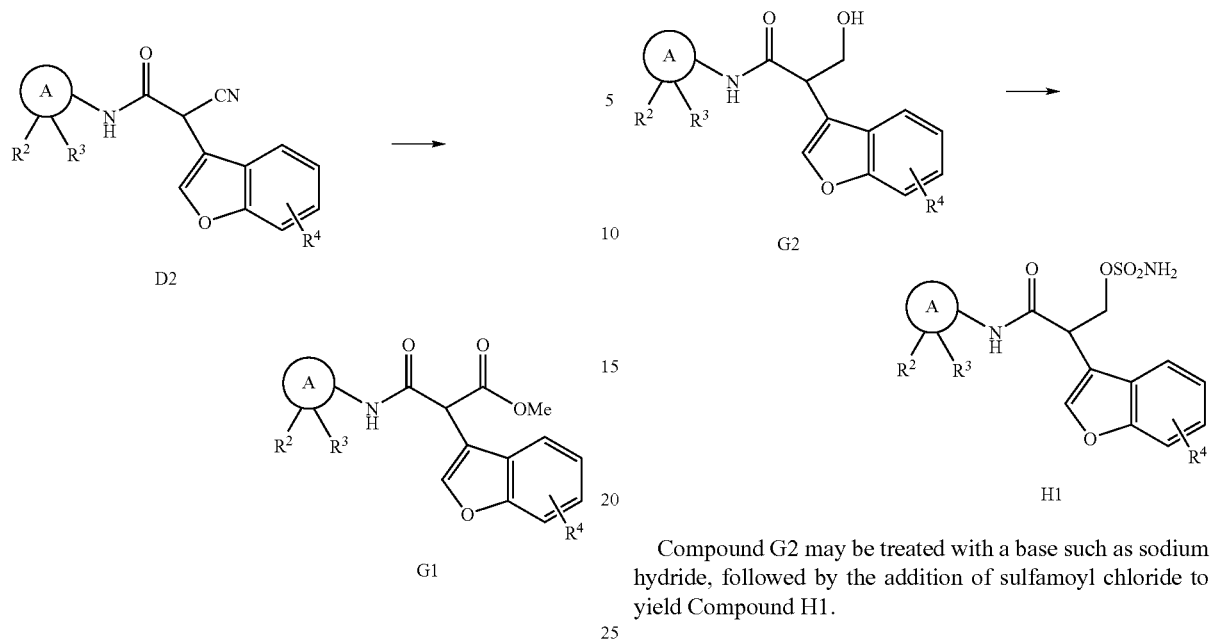

Nitrile Compound D2 may be converted to an imidate in the presence of HCl gas, followed by hydrolysis to yield Compound G1.

Compound G1 may be reduced to a primary alcohol in the presence of hydride source, such as sodium borohydride, to give methyl alcohol Compound G2.

Scheme H

Scheme H illustrates the preparation of compounds representative of the present invention wherein Y of Formula (I) is a sulfamic acid methyl group.

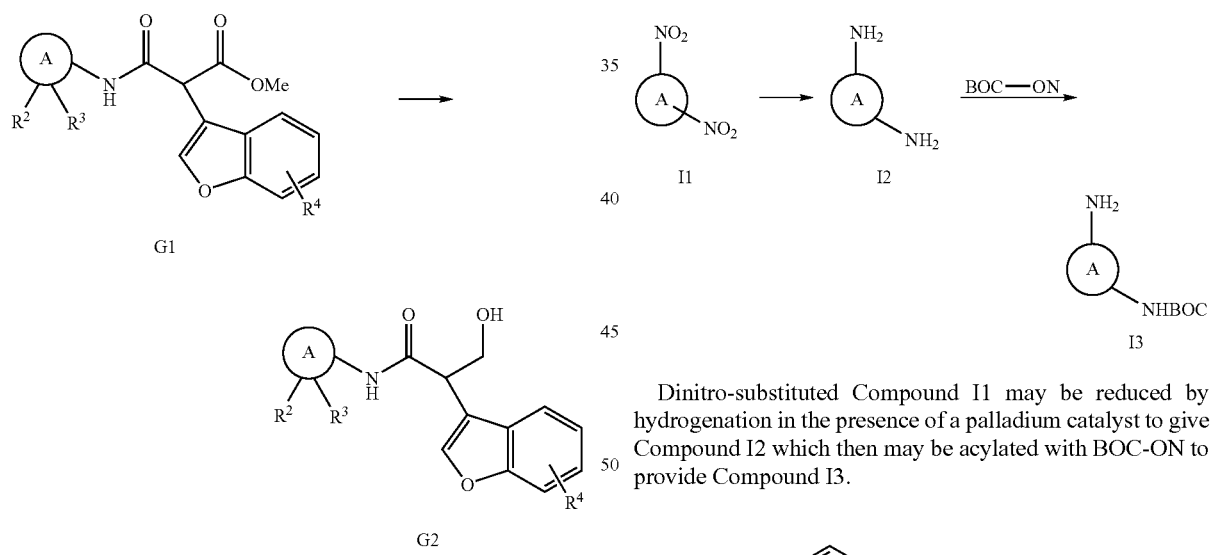

Compound G2 may be treated with a base such as sodium hydride, followed by the addition of sulfamoyl chloride to yield Compound H1.

Scheme I

Scheme I illustrates the general method for the preparation of compounds representative of the present invention wherein $R^3$ is an amide substituent on ring A as defined by the invention.

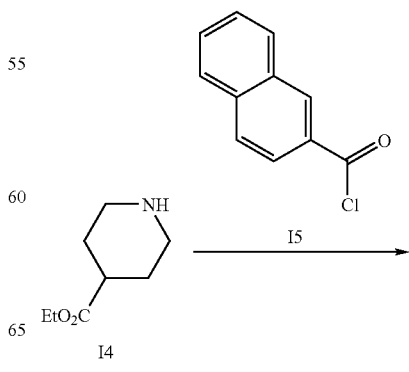

Dinitro-substituted Compound I1 may be reduced by hydrogenation in the presence of a palladium catalyst to give Compound I2 which then may be acylated with BOC-ON to provide Compound I3.

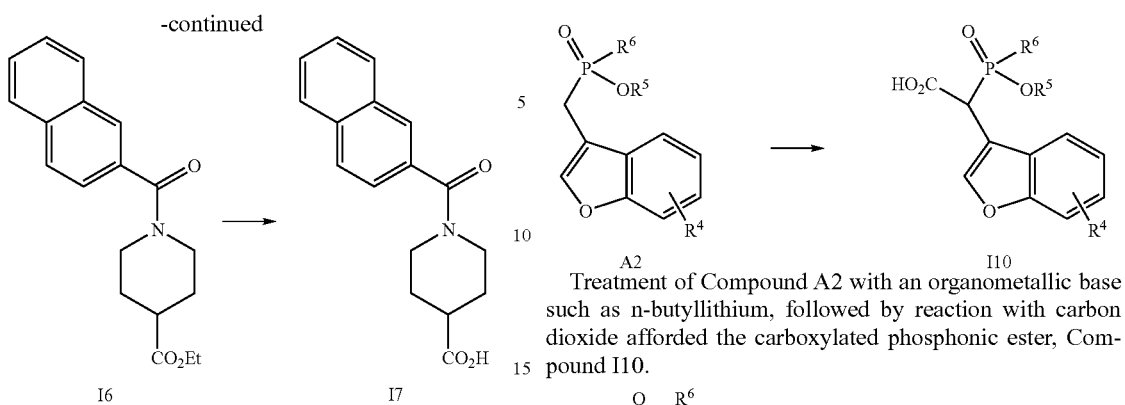

Compound I4 may be acylated with acid chloride Compound I5 to yield Compound I6, followed by saponification of Compound I6 (using a reagent such as LiOH) to provide carboxylic acid Compound I7.

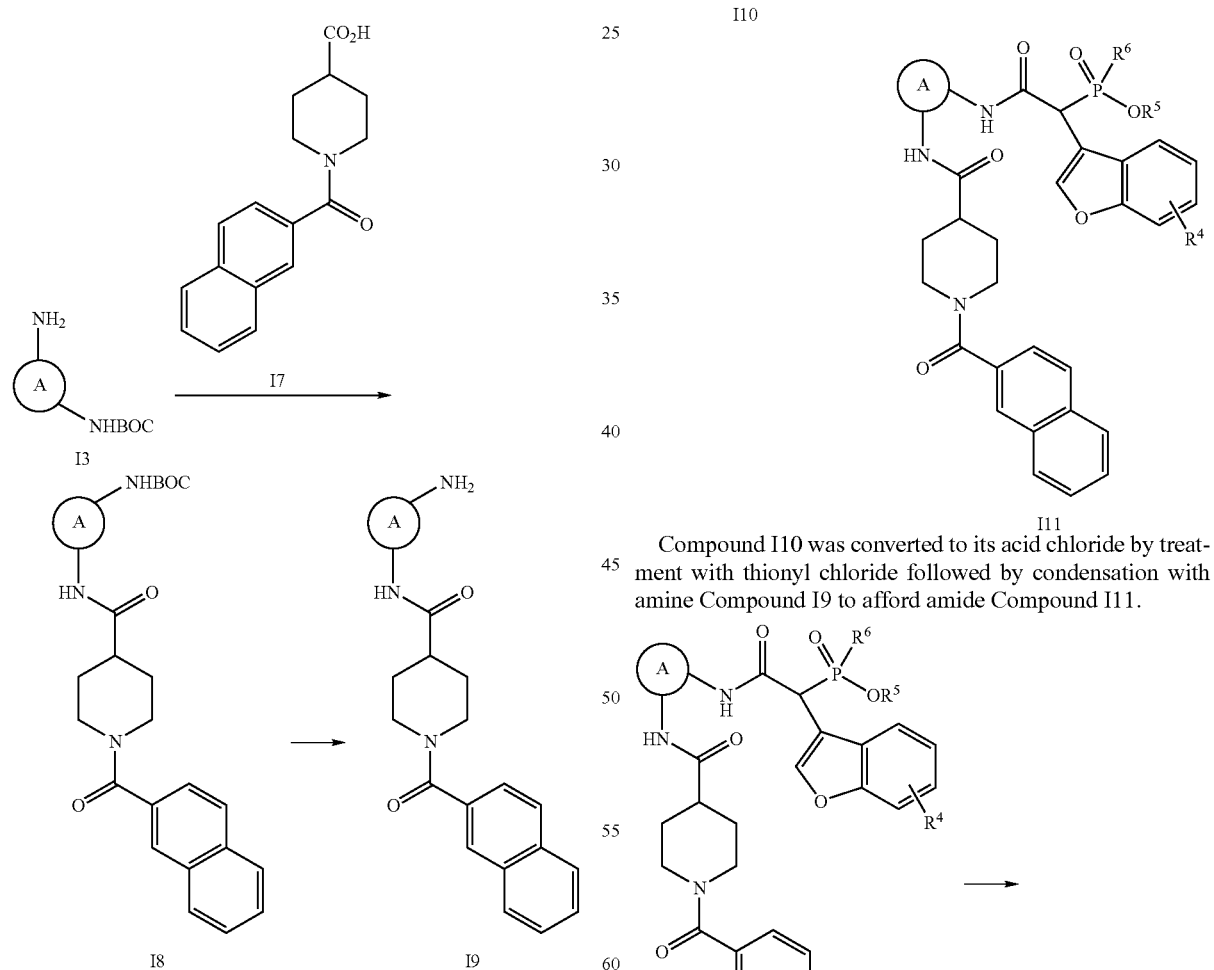

Compound I8 may be prepared by coupling Compound I3 to Compound I7 using an appropriate coupling agent, activating agent, and solvent. The Boc protecting group of Compound I8 was removed under acidic conditions to afford the free amine, Compound I9.

Treatment of Compound A2 with an organometallic base such as n-butyllithium, followed by reaction with carbon dioxide afforded the carboxylated phosphonic ester, Compound I10.

Compound I10 was converted to its acid chloride by treatment with thionyl chloride followed by condensation with amine Compound I9 to afford amide Compound I11.

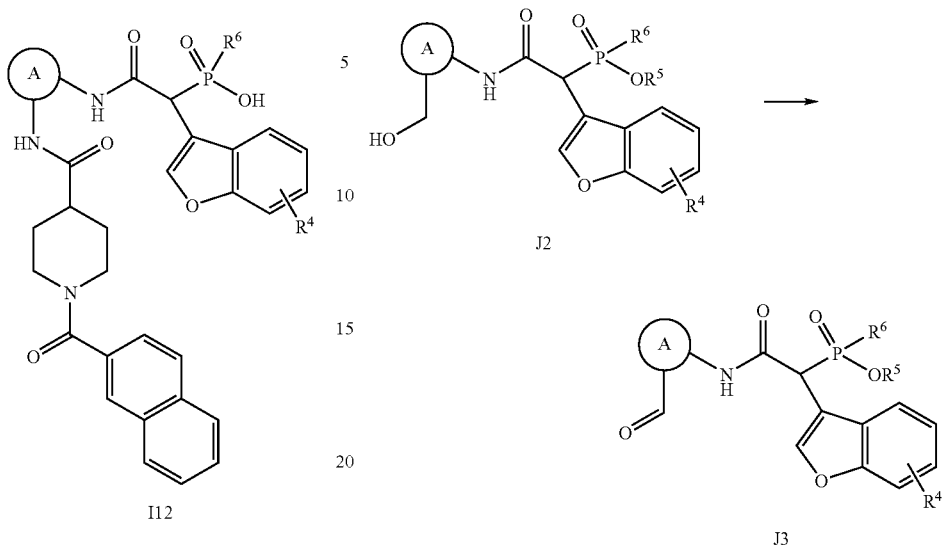

Compound I11 was dealkylated using bromotrimethylsilane and treated with HCl to provide Compound I12.

Scheme J

Scheme J illustrates a method for the preparation of compounds representative of the present invention.

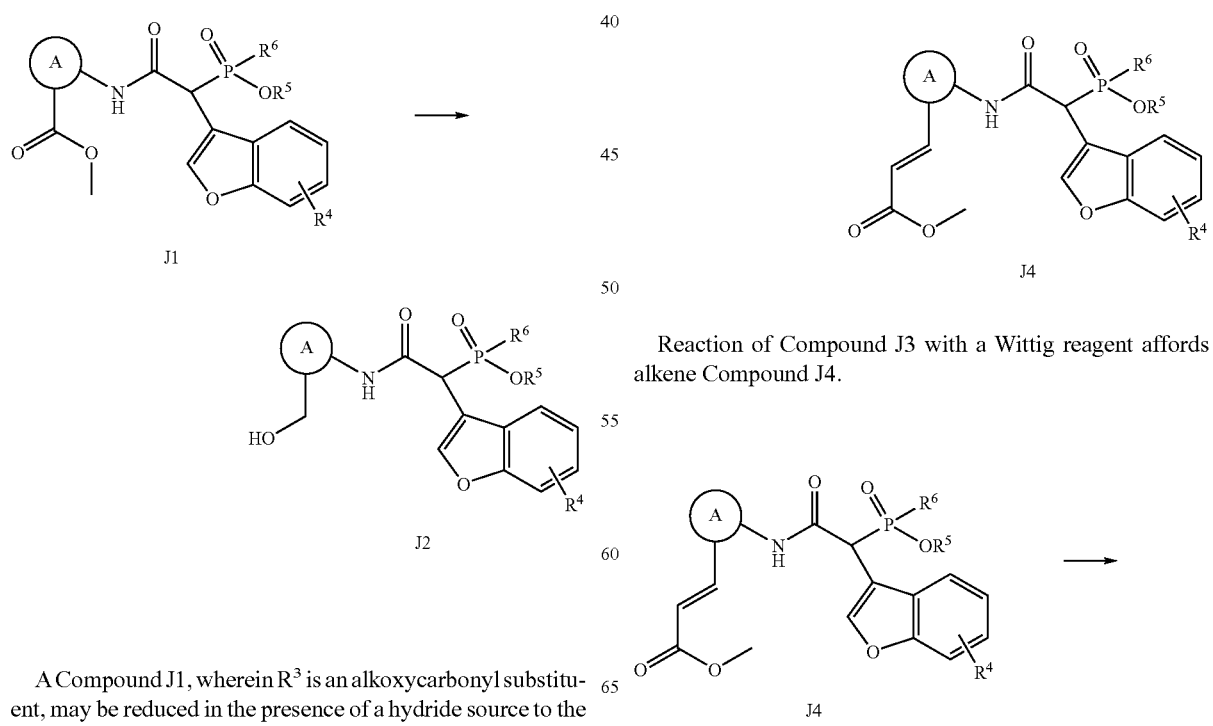

A Compound J1, wherein $R^3$ is an alkoxycarbonyl substituent, may be reduced in the presence of a hydride source to the corresponding alcohol, Compound J2.

Compound J2 may be oxidized to aldehyde Compound J3.

Reaction of Compound J3 with a Wittig reagent affords alkene Compound J4.

-continued

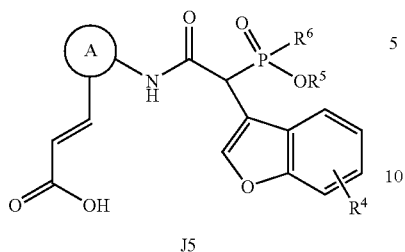
J5

Saponification of Compound J4 provides carboxylic acid Compound J5.

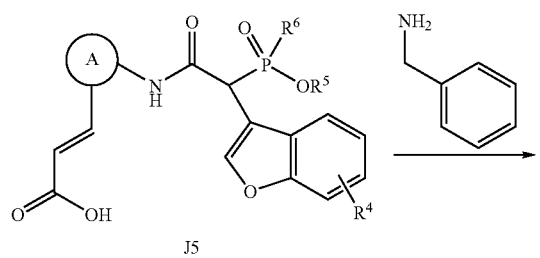
J5

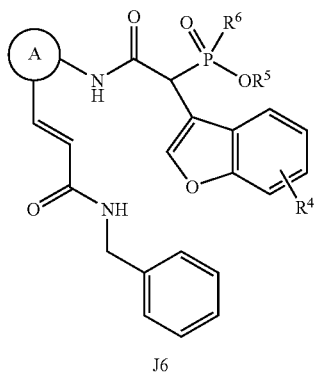
J6

Compound J5 may be coupled with an amine, such as benzyl amine, in the presence of an appropriate coupling agent as described supra, to give amide Compound J6.

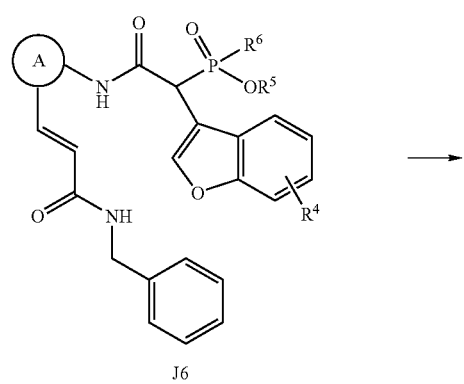
J6

-continued

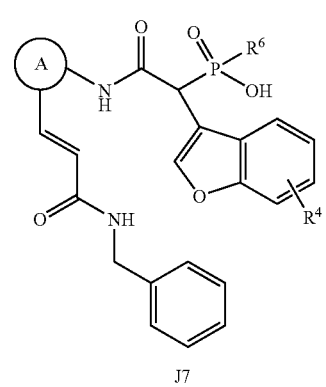
J7

Compound J6 may be dealkylated using the procedure previously described in Scheme A to yield Compound J7.

Alternatively, other compounds of the present invention wherein $R^3$ is alkoxy or —C(=O)NR$^{11}$R$^{12}$ may be derived from Compound J2. The hydroxy group of Compound J2 may be alkylated using reagents and methods known to one skilled in the art to afford compounds wherein $R^3$ is alkoxy.

Alternatively, the hydroxy group of Compound J2 may be reacted with a variety of acylating agents known to one skilled in the art, such as isocyanates, to arrive at compounds of the present invention wherein $R^3$ is a carbamate.

Scheme K

Scheme K illustrates a method for the preparation of compounds representative of the present invention.

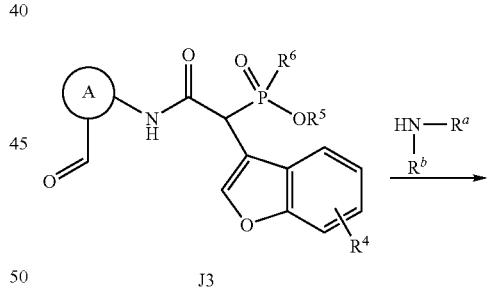
J3

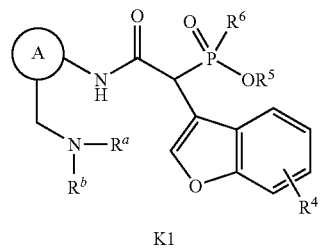
K1

As shown in Scheme K, Compound J3 may be reacted with a variety of amines in the presence of a hydride source under acidic conditions to yield Compound K1.

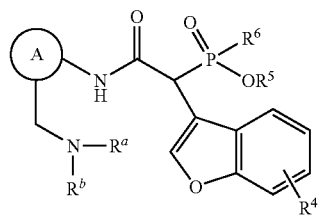

K1

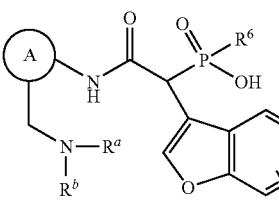

K2

Dealkylation of Compound K1 by the method described in Scheme A affords Compound K2.

Scheme L

The preparation of compounds representative of the present invention wherein $R^3$ is —C(=O)Cy, as previously defined, and said Cy is attached through a nitrogen atom, is shown in Scheme L.

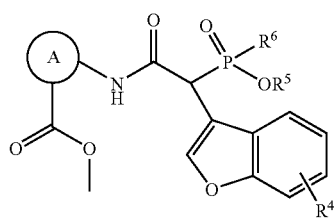

J1

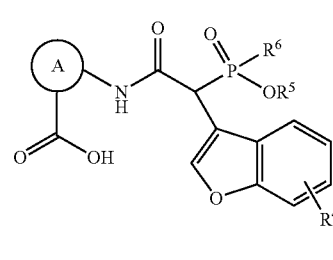

L1

Compound J1 may be saponified under basic conditions to provide Compound L1 (wherein Ring A is phenyl or naphthyl).

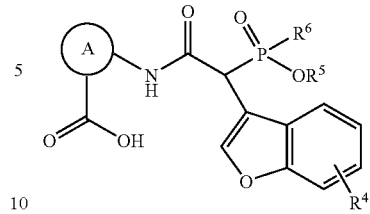

L1

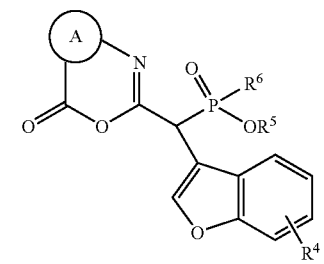

L2

Compound L1 may be treated with thionyl chloride to give Compound L2.

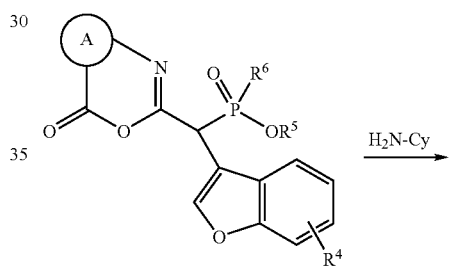

L2

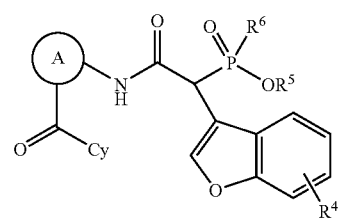

L3

Compound L2 may be reacted with a substituted amine (wherein Cy is as previously defined) to provide Compound L3.

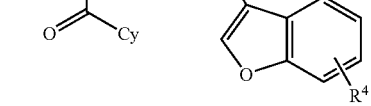

L3

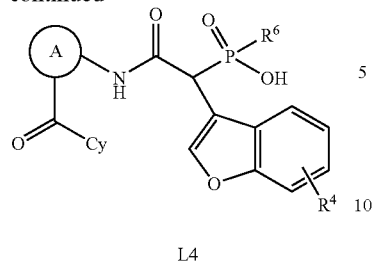

L4

Dealkylation of Compound L3 using methods previously described affords Compound L4.

Scheme M

Scheme M illustrates a method for the preparation of compounds representative of the present invention wherein $R^5$ and $R^6$ are appropriately substituted alkoxy substituents as defined herein.

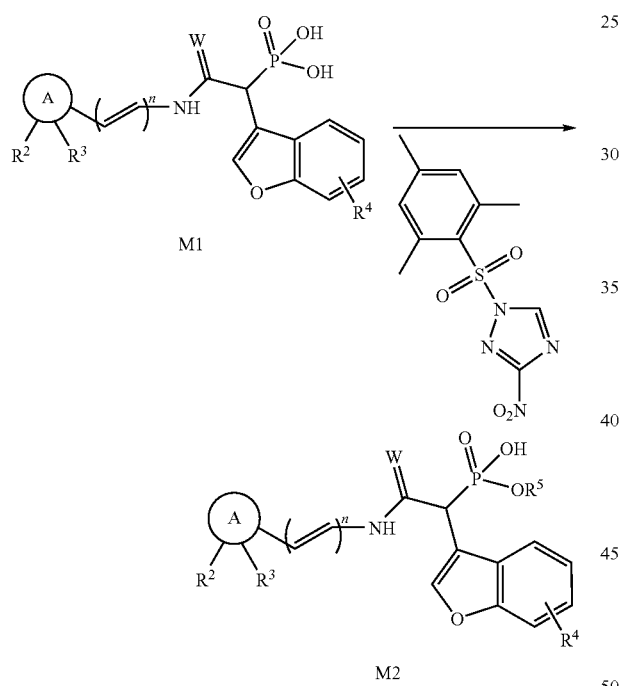

A compound of formula M1 wherein $R^5$ is hydrogen and $R^6$ is hydroxy may be coupled with an appropriately substituted alcohol in the presence of MSNT (1-(mesitylene-2-sulfonyl)-3-nitro-1,2,4-triazole) to afford a compound of formula M2 wherein $R^5$ is a substituted alkyl and $R^6$ is a substituted alkoxy as defined herein.

Alternatively, compounds of formula M1 may be elaborated using an appropriately substituted alkylating agent to provide compounds of the present invention where either one or both hydroxy groups of the phosphonic acid are alkylated. An alkylating agent in this instance is an alkyl substituent that is optionally substituted as defined for $R^5$ or $R^6$, and said alkyl substituent is substituted with a leaving group. A leaving group is defined as a substituent that is activated toward nucleophilic displacement, including halides, tosylates, and the like.

Scheme N

Scheme N illustrates the preparation of compounds representative of the present invention wherein $R^5$ and $R^6$ (when $R^6$ is alkoxy) are taken together with the atoms to which they are both attached to form a monocyclic ring.

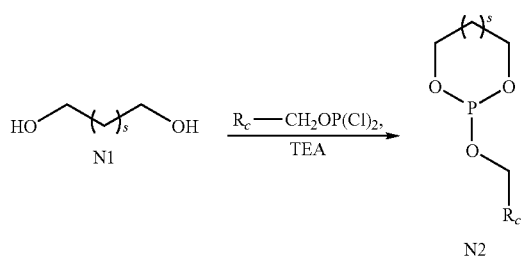

A diol of formula N1 (wherein s is 0, 1 or 2) may be treated with a dichlorophosphite (wherein Rc is benzyl- or lower alkyl-) to form a cyclic phosphonate of formula N2.

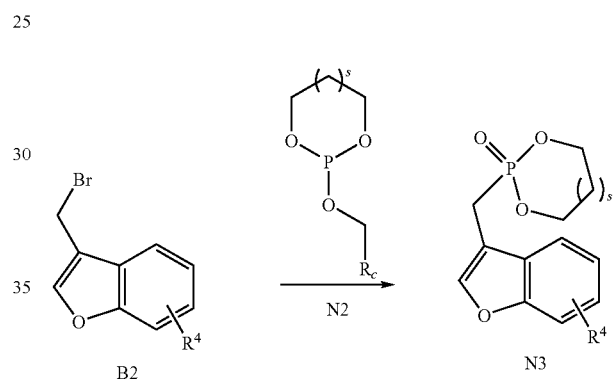

A compound of formula N2 may be condensed under refluxing conditions with a compound of formula B2 to form a compound of formula N3.

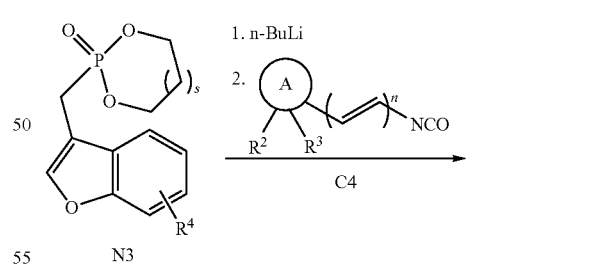

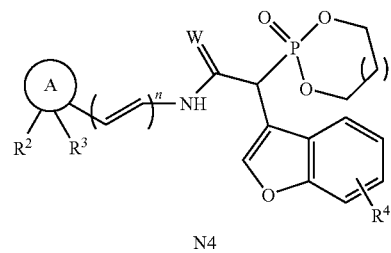

N4

The elaboration of a compound of formula N3 to a compound of formula N4 may be achieved using the methods described for Scheme A.

SPECIFIC SYNTHETIC EXAMPLES

The following Examples are set forth to aid in the understanding of the invention, and are not intended and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a Bruker AC® 300B (300 MHz proton) or a Bruker® AM-400 (400 MHz proton) spectrometer with Me$_4$Si as an internal standard (s=singlet, d=doublet, m=multiplet, t=triplet, br=broad). ES-MS were recorded on a Micromass® mass spectrometer or on an Agilent® HPLC mass spectrometer. TLC was performed with Whatman® 250-µm silica gel plates. Preparative TLC was performed with Analtech® tapered silica gel GF plates. Preparative HPLC separations were carried out on a Gilson® HPLC using a Phenomenex® Kromasil 100 A C18 column (25 cm×50 mm, or 10 cm×21.2 mm) using gradients of CH$_3$CN/water/ 0.2% TFA; Analytical HPLC separations were carried out on a Supelco® ABZ+Plus column (5 cm×2.1 mm) or a YMC® J'Sphere H80 S4 column (5 cm×2 mm) with detection at 220 nm and 254 nm on a Hewlett Packard® 1100 UV detector. The gradient used was 10% to 90% CH$_3$CN/water/0.1% TFA in 6 min. Reported percent purity data is based on the 220 nm data. Microanalysis was performed by Robertson Microlit Laboratories, Inc.

Example 1

[Benzofuran-3-yl-(naphthalen-2-ylcarbamoyl)-methyl]-phosphonic acid (Cpd 1)

Compound 1d was prepared according to a procedure described in *J. Med. Chem.*, 1997, 40 (17) 2706-2725, as follows:

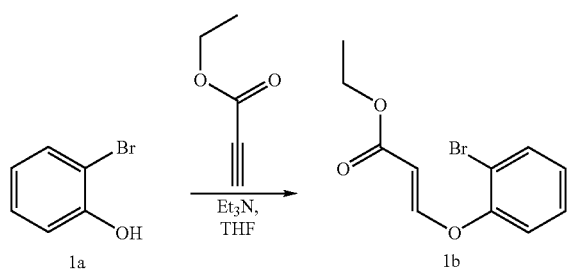

Compound 1a was reacted with ethyl propiolate in the presence of TEA and THF at room temperature to provide Compound 1b.

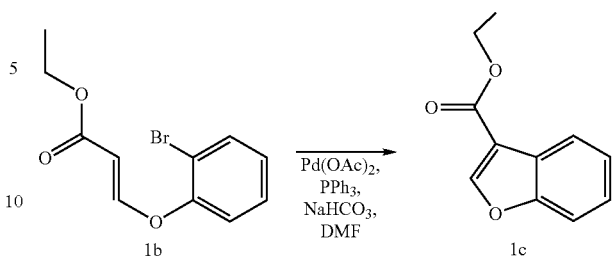

Compound 1b was reacted in the presence of Pd(OAc)$_2$ and PPH$_3$ and a base NaHCO$_3$ in DMF at 110° C. for 16 h to provide Compound 1c.

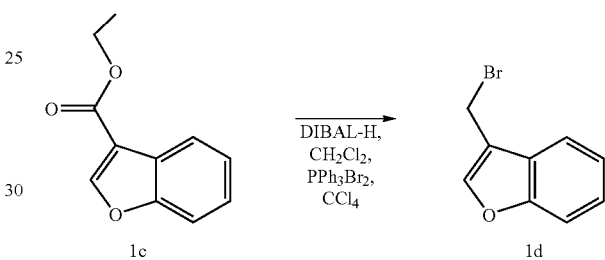

Compound 1c was reacted with a solution of DIBAL-H in CH$_2$Cl$_2$ at −78° C. and allowed to warm to RT to provide an intermediate which was not isolated. The intermediate was reacted in the presence of PPh$_3$Br$_2$ and CCl$_4$ at −0° C. to provide Compound 1d.

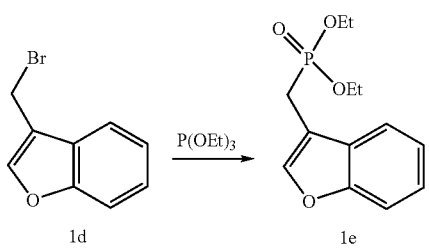

To a solution of Compound 1d (0.29 g; 1.36 mmol) in 10 mL of dry toluene was added triethylphosphite (1.35 mL; 7.8 mmol) and the solution was heated at reflux for a total of 23 h. The reaction was concentrated under high vacuum (<0.5 mTorr) at 90° C. The crude product was purified by flash column (EtOAc/heptane gradient) to yield 0.30 g of Compound 1e as a clear viscous oil (HPLC: 100% 3.09 min.; MS (ES): MH$^+$=269).

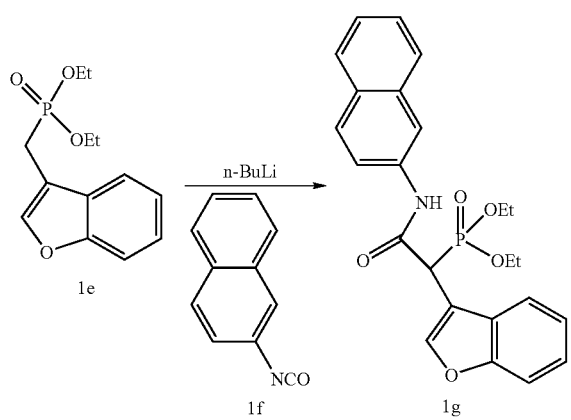

To a solution of n-butyllithium (1.49 mmol) in 7 mL of dry THF under Ar at −78° C. was added a solution of Compound 1e (0.30 g; 1.10 mmol) in 7 mL of dry THF dropwise. The yellow solution was stirred at −78° C. for 45 min, and a mixture of 2-napthyl isocyanate Compound 1f (0.20 g; 1.21 mmol) in 7 mL of dry THF was added dropwise. The reaction was allowed to warm slowly in a dry ice/acetone bath for 2 h before being quenched with saturated aqueous NH$_4$Cl (2 mL). The mixture was warmed to rt, and water was added until two clear layers appeared. The layers were separated, and the aqueous portion was extracted three times with 5 mL of EtOAc. The combined organics were washed once with 10 mL of brine and dried over Na$_2$SO$_4$. The mixture was filtered, the organics were concentrated under reduced pressure, and the crude product was triturated with MeCN to yield Compound 1g (0.29 g) as a white solid. HPLC: 100% 3.93 min. retention time; MS (ES): MH$^+$=438.

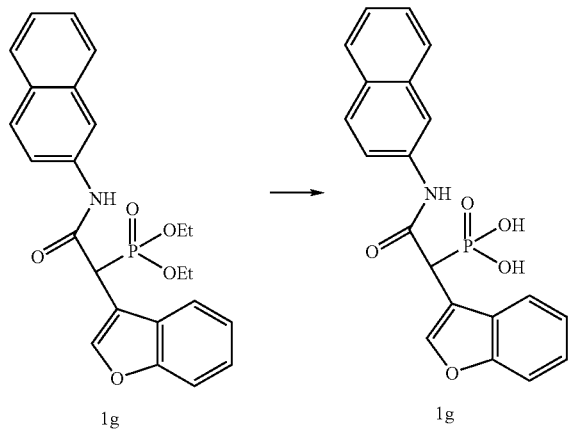

To a solution of Compound 1g (0.29 g; 0.65 mmol) in 5 mL of dry pyridine was added TMS-Br (0.69 mL; 5.24 mmol) in three portions, 15 min apart. After 90 min total reaction time, the reaction mixture was concentrated, and MeOH and 1N HCl were added to give a clear solution. The solution was concentrated, and the residue stirred for 1 h in 1N HCl. The solid was collected and dried in a filter funnel under N$_2$., then resuspended in MeCN, stirred for 45 min, then collected. A second crop was isolated from the filtrate in the same manner, and the combined product was suspended in a small volume of MeOH and tromethamine (1 equivalent; 63 mg) was added to yield a clear solution. The solution was filtered and concentrated under reduced pressure, and the crude salt was recrystallized from MeCN containing a small amount of EtOAc to yield Compound 1 as a white powder. HPLC: 3.75 min. retention time; MS (ES) MH$^+$=382; $^1$H NMR (DMSO-d$_6$) δ 4.30 (d, 1H, J=21.8 Hz), 7.12-7.16 (m, 1H), 7.21-7.26 (m, 1H), 7.32-7.45 (m, 2H), 7.49-7.58 (m, 2H), 7.72-7.80 (m, 2H), 7.98 (d, 1H, J=2.2 Hz), 8.26 (d, 1H, J=1.1 Hz), 11.44 (s, 1H).

Using the procedure of Example 1 and appropriate starting materials, reagents and conditions known to those skilled in the art, other compounds or an enantiomer, diastereomer, polymorph or pharmaceutically acceptable salt thereof, which are representative of the present invention may be prepared:

| Cpd | Name |
|---|---|
| 2 | [(5-methyl-benzofuran-3-yl)-(naphthalen-2-ylcarbamoyl)-methyl]-phosphonic acid |
| 3 | [(5-methoxy-benzofuran-3-yl)-(naphthalen-2-ylcarbamoyl)-methyl]-phosphonic acid |
| 4 | [(6-methoxy-benzofuran-3-yl)-(naphthalen-2-ylcarbamoyl)-methyl]-phosphonic acid |
| 5 | [(5,7-dibromo-benzofuran-3-yl)-(naphthalen-2-ylcarbamoyl)-methyl]-phosphonic acid |
| 6 | [(5,7-dibromo-6-methyl-benzofuran-3-yl)-(naphthalen-2-ylcarbamoyl)-methyl]-phosphonic acid |
| 7 | [(5,7-dibromo-6-methoxy-benzofuran-3-yl)-(naphthalen-2-ylcarbamoyl)-methyl]-phosphonic acid |
| 8 | [(5-chloro-benzofuran-3-yl)-(naphthalen-2-ylcarbamoyl)-methyl]-phosphonic acid |
| 9 | [(4-hydroxy-benzofuran-3-yl)-(naphthalen-2-ylcarbamoyl)-methyl]-phosphonic acid |
| 10 | [(5-bromo-benzofuran-3-yl)-(naphthalen-2-ylcarbamoyl)-methyl]-phosphonic acid |
| 11 | [(7-methoxy-benzofuran-3-yl)-(naphthalen-2-ylcarbamoyl)-methyl]-phosphonic acid |
| 12 | [(5-hydroxy-benzofuran-3-yl)-(naphthalen-2-ylcarbamoyl)-methyl]-phosphonic acid |
| 13 | [benzofuran-3-yl-(naphthalen-2-ylcarbamoyl)-methyl]-methyl-phosphinic acid |
| 14 | methyl-[(5-methyl-benzofuran-3-yl)-(naphthalen-2-ylcarbamoyl)-methyl]-phosphinic acid |
| 15 | [(5-methoxy-benzofuran-3-yl)-(naphthalen-2-ylcarbamoyl)-methyl]-methyl-phosphinic acid |
| 16 | [(6-methoxy-benzofuran-3-yl)-(naphthalen-2-ylcarbamoyl)-methyl]-methyl-phosphinic acid |
| 17 | [(5,7-dibromo-benzofuran-3-yl)-(naphthalen-2-ylcarbamoyl)-methyl]-methyl-phosphinic acid |
| 18 | [(5,7-dibromo-6-methyl-benzofuran-3-yl)-(naphthalen-2-ylcarbamoyl)-methyl]-methyl-phosphinic acid |
| 19 | [(5,7-dibromo-6-methoxy-benzofuran-3-yl)-(naphthalen-2-ylcarbamoyl)-methyl]-methyl-phosphinic acid |
| 20 | [(5-chloro-benzofuran-3-yl)-(naphthalen-2-ylcarbamoyl)-methyl]-methyl-phosphinic acid |
| 21 | [(4-hydroxy-benzofuran-3-yl)-(naphthalen-2-ylcarbamoyl)-methyl]-methyl-phosphinic acid |
| 22 | [(5-bromo-benzofuran-3-yl)-(naphthalen-2-ylcarbamoyl)-methyl]-methyl-phosphinic acid |
| 23 | [(7-methoxy-benzofuran-3-yl)-(naphthalen-2-ylcarbamoyl)-methyl]-methyl-phosphinic acid |
| 24 | [(5-hydroxy-benzofuran-3-yl)-(naphthalen-2-ylcarbamoyl)-methyl]-methyl-phosphinic acid |

BIOLOGICAL EXPERIMENTAL EXAMPLES

The utility of the compounds of the present invention as a serine protease inhibitor and, particularly, as a chymase inhibitor useful for the treatment of inflammatory or serine protease mediated disorders can be determined according to the procedures described herein.

Example 1

Enzyme-Catalyzed Hydrolysis Assays

Enzyme-catalyzed hydrolysis rates were measured spectrophotometrically using human skin chymase (Cortex Biochem), a chromogenic substrate (Suc-Ala-Ala-Pro-Phe-pNa) (Bachem) in aqueous buffer (450 mM Tris, 1800 mM NaCl, pH 8.0), and a microplate reader (Molecular Devices). $IC_{50}$ experiments were conducted by fixing the enzyme and substrate concentrations (10 nM enzyme, 0.7 mM substrate) and varying the inhibitor concentration. Changes in absorbance at 405 nM were monitored using the software program Softmax (Molecular Devices), upon addition of enzyme, with and without inhibitor present at 37° C. for 30 minutes. Percent inhibition was calculated by comparing the initial reaction slopes of the samples without inhibitor to those with inhibitor.

The $IC_{50}$ value (2.54±0.56 µM; N=4) for Compound 1 as a chymase inhibitor was determined using a four parameter fit logistics model.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of Formula (I)

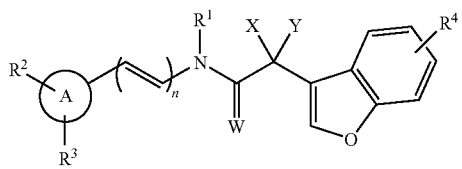

wherein
 $R^1$ is selected from the group consisting of hydrogen and $C_{1-4}$alkyl;
 Ring A is selected from the group consisting of aryl, heteroaryl, benzo fused heterocyclyl, cycloalkyl and benzo fused cycloalkyl;
 $R^2$ is one, two or three substituents independently selected from the group consisting of hydrogen, $C_{1-6}$alkyl, $C_{2-6}$alkenyl, $C_{2-6}$alkynyl, $C_{1-6}$alkoxy, —OCH$_2$—C$_{2-6}$ alkenyl, $C_{1-6}$alkylthio, —OCF$_3$, —NH$_2$, —NH(C$_{1-6}$) alkyl, —N(C$_{1-6}$)dialkyl, aryl, heteroaryl, aryloxy, heteroaryloxy, halogen, hydroxy and nitro,
  wherein, $R^2$ is optionally oxo when Ring A is heteroaryl or benzo fused heterocyclyl,
  wherein any aryl-containing substituent of $R^2$ is optionally substituted with a substituent independently selected from the group consisting of $C_{1-6}$alkyl, $C_{1-6}$alkoxy, $C_{2-6}$alkenyl, $C_{1-6}$alkylthio, —NH$_2$, —NH(C$_{1-6}$)alkyl, —N(C$_{1-6}$)dialkyl, aryl, heteroaryl, aryloxy, heteroaryloxy, halogen, hydroxy and nitro, and
  wherein any of the foregoing $C_{1-6}$alkyl, $C_{2-6}$alkenyl or $C_{1-6}$ alkoxy containing substituents of $R^2$ are optionally substituted with a substituent independently selected from the group consisting of —NR$^{11}$R$^{12}$, aryl, heteroaryl, one, two or three halogen atoms and hydroxy;
 $R^{11}$ and $R^{12}$ are independently hydrogen; $C_{1-6}$ alkyl optionally substituted with hydroxy, aryl, —C(=O)C$_{1-4}$ alkoxy, or NR$^{15}$R$^{16}$; or aryl;
 $R^{15}$ and $R^{16}$ are substituents independently selected from the group consisting of hydrogen, $C_{1-6}$alkyl and aryl; optionally, $R^{15}$ and $R^{16}$ are each taken together with the atoms to which they are attached to form a ring of five to seven members;
 $R^3$ is one, two or three substituents independently selected from the group consisting of hydrogen, $C_{1-6}$alkyl, $C_{2-6}$alkenyl, $C_{2-6}$alkynyl, $C_{1-6}$alkoxy, $C_{1-6}$alkylthio, —OCF$_3$, —OCH$_2$(C$_{2-6}$)alkenyl, —NH$_2$, —NH(C$_{1-6}$) alkyl, —N(C$_{1-6}$)dialkyl, —NHC(=O)Cy, —N(C$_{1-6}$ alkyl)C(=O)Cy, —(NC(=O))$_2$NH$_2$, —C(=O)C$_{1-4}$ alkoxy, —C(=O)NR$^{17}$R$^{18}$, —C(=O)NHcycloalkyl, —C(=O)N(C$_{1-6}$alkyl)cycloalkyl, —C(=O)NHCy, —C(=O)N(C$_{1-6}$alkyl)Cy, —C(=O)Cy, —OC(=O) C$_{1-6}$alkyl, —OC(=O)NR$^{19}$R$^{20}$, —C(=O)Oaryl, —C(=O)Oheteroaryl, —CO$_2$H, ureido, halogen, hydroxy, nitro, cyano, aryl, heteroaryl, heteroaryloxy and aryloxy,
  wherein any of the foregoing $C_{1-6}$alkyl or $C_{1-6}$ alkoxy containing substituents of $R^3$ are optionally substituted with one, two or three substituents independently selected from the group consisting of —NR$^{21}$R$^{22}$, —NH(cycloalkyl), —N(C$_{1-6}$alkyl)(cycloalkyl), —NHCy, —N(C$_{1-6}$alkyl)Cy, —NHC(O)—C$_{1-6}$alkyl—C$_{1-6}$alkoxy, aryl, heteroaryl, hydroxy, halogen, —C(=O)NR$^{23}$R$^{24}$, —OC(=O)NR$^{25}$R$^{26}$, —C(=O)C$_{1-4}$alkoxy, and —C(=O)Cy;
  wherein any of the foregoing $C_{2-6}$alkenyl and $C_{2-6}$alkynyl containing substituents of $R^3$ are optionally substituted with aryl or —C(=O)NR$^{27}$R$^{28}$, and
  wherein the aryl, heteroaryl and cycloalkyl substituents of $R^3$ are optionally substituted with one, two or to three substituents independently selected from $R^{14}$;
 $R^{14}$ is independently hydrogen, $C_{1-6}$alkyl, $C_{1-6}$alkoxy, $C_{2-6}$alkenyl, $C_{1-6}$alkylthio, —NH$_2$, —NH(C$_{1-6}$)alkyl, —N(C$_{1-6}$)dialkyl, aryl, heteroaryl, aryloxy, heteroaryloxy, halogen, hydroxy, or nitro;
  wherein each of the $C_{1-6}$alkyl- or $C_{1-6}$alkoxy-containing substituents of $R^{14}$ is optionally substituted on a terminal carbon atom with a substituent selected from —NR$^{29}$R$^{30}$, aryl, heteroaryl, one, two or three halogen atoms, or hydroxy;
 $R^{17}$, $R^{18}$, $R^{19}$, $R^{20}$, $R^{21}$, $R^{22}$, $R^{23}$, $R^{24}$, $R^{25}$ and $R^{26}$ are substituents independently selected from the group consisting of hydrogen, $C_{1-6}$ alkyl, and aryl,
 wherein $C_{1-6}$alkyl and aryl are each optionally substituted with hydroxy, aryl, aryloxy, —C(=O)-aryl, —C(=O) C$_{1-4}$alkoxy, NH$_2$, —NH(C$_{1-6}$alkyl), or —N(C$_{1-6}$)dialkyl; optionally, $R^{17}$ and $R^{18}$, $R^{19}$ and $R^{20}$, $R^{21}$ and $R^{22}$, $R^{23}$ and $R^{24}$, or $R^{25}$ and $R^{26}$ are each taken together with the atoms to which they are attached to form a ring of five to seven members;
 $R^{27}$ and $R^{28}$ are independently hydrogen; $C_{1-6}$ alkyl optionally substituted with hydroxy, aryl, —C(=O)C$_{1-4}$ alkoxy, NH$_2$, —NH(C$_{1-6}$alkyl), or —N(C$_{1-6}$)dialkyl; or aryl; optionally, $R^{27}$ and $R^{28}$ are each taken together with the atoms to which they are attached to form a ring of five to seven members;
 $R^{29}$ and $R^{30}$ are independently hydrogen, $C_{1-6}$alkyl aryl, wherein $C_{1-6}$alkyl is optionally substituted with hydroxy, aryl, —C(=O)C$_{1-4}$alkoxy, NH$_2$, —NH(C$_{1-6}$ alkyl), or —N(C$_{1-6}$)dialkyl, and, optionally, R$^{29}$ and R$^{30}$ are each taken together with the atoms to which they are attached to form a ring of five to seven members;

Cy is a heterocyclyl optionally substituted with a substituent selected from the group consisting of oxo, C$_{1-6}$alkyl, —C$_{1-6}$alkylC(═O)C$_{1-6}$alkyl, —C$_{1-6}$alkylC(═O)C$_{1-6}$alkoxy, —C$_{1-6}$alkyl-aryl, —C$_{1-6}$alkylC(═O)aryl, —C(═O)(C$_{1-6}$)alkyl, —C(═O)(C$_{1-6}$)alkoxy, —C(═O)aryl, —SO$_2$aryl, aryl, heteroaryl, and heterocyclyl, wherein the aryl portion of any aryl-containing substituent of Cy is optionally substituted with one, two or three substituents independently selected from the group consisting of C$_{1-6}$alkyl, C$_{1-6}$alkoxy, C$_{1-6}$alkylthio, halogen, hydroxy, NH$_2$, —NH(C$_{1-6}$alkyl), and —N(C$_{1-6}$)dialkyl, and wherein heterocyclyl is optionally substituted with aryl, one, two or three halogen atoms, or one, two or three oxo substituents; and heterocyclyl is optionally spiro-fused to said Cy;

n is 0 or 1;

W is O or S;

X is hydrogen or C$_{1-3}$alkyl;

Y is independently selected from the group consisting of C$_{1-6}$alkyl substituted with —OSO$_2$NH$_2$ or hydroxy; SO$_3$H, CO$_2$H, heteroaryl, —OC(═O)NH$_2$, and P(═O)OR$^5$R$^6$; provided that when Y is CO$_2$H, Ring A must be a bicyclic ring system;

R$^5$ is selected from the group consisting of hydrogen; C$_{1-6}$alkyl and aryl, wherein C$_{1-6}$alkyl is optionally substituted with NH$_2$, —NH(C$_{1-6}$)alkyl, —N(C$_{1-6}$)dialkyl, 1,3-dioxolan-2-yl, C$_{1-6}$alkylcarbonyloxy-, C$_{1-6}$alkoxycarbonyloxy-, C$_{1-6}$alkylcarbonylthio-, (C$_{1-6}$)alkylaminocarbonyl-, di(C$_{1-6}$)alkylaminocarbonyl-, one, two or three halogen atoms, or hydroxy, and wherein aryl is optionally substituted with C$_{1-6}$alkyl, C$_{1-6}$alkoxy, C$_{1-6}$alkylthio, C$_{2-6}$alkenyl, —NH$_2$, —NH(C$_{1-6}$)alkyl, —N(C$_{1-6}$)dialkyl, aryl, heteroaryl, aryloxy, heteroaryloxy, halogen, hydroxy, or nitro, and, optionally, when R$^6$ is C$_{1-8}$alkoxy, R$^5$ and R$^6$ may each be taken together with the atoms to which they are attached to form a 5-8 membered monocyclic ring;

R$^6$ is selected the group consisting of C$_{1-8}$alkyl, C$_{1-8}$alkoxy, C$_{2-8}$alkenyl, heteroaryl, aryl, and hydroxy, wherein C$_{1-8}$alkyl, C$_{1-8}$alkoxy, and C$_{2-8}$alkenyl are optionally substituted with a substituent selected from the group consisting of C$_{1-6}$alkoxy, aryl, heterocyclyl, heteroaryl, NH$_2$, —NH(C$_{1-6}$)alkyl, —N(C$_{1-6}$)dialkyl, C$_{1-6}$alkylcarbonyloxy-, C$_{1-6}$alkylcarbonylthio-, C$_{1-6}$alkoxycarbonyloxy-, (C$_{1-6}$)alkylaminocarbonyl-, di(C$_{1-6}$)alkylaminocarbonyl-, one, two or three halogen atoms and hydroxy, wherein when R$^6$ is C$_{1-8}$alkyl, said C$_{1-8}$alkyl is optionally substituted with halogen selected from up to three chlorine atoms or up to seven fluorine atoms, and wherein the heteroaryl and aryl substituents of R$^6$ are optionally substituted with a substituent independently selected from the group consisting of C$_{1-6}$alkyl, C$_{1-6}$alkoxy, C$_{2-6}$alkenyl, C$_{1-6}$alkylthio, —NH$_2$, —NH(C$_{1-6}$)alkyl, —N(C$_{1-6}$)dialkyl, aryl, heteroaryl, aryloxy, heteroaryloxy, halogen, hydroxy and nitro;

R$^4$ is one, two or three substituents selected from the group consisting of hydrogen, C$_{1-6}$alkyl, C$_{2-6}$alkenyl, C$_{1-6}$alkoxy, C$_{1-6}$alkylthio, aryl(C$_{1-6}$)alkyl, aryl(C$_{2-6}$)alkenyl, halogen, hydroxy, —C(═O)Cy, —C(═O)NR$^{31}$R$^{32}$, aryl, —CO$_2$H, oxo and cyano, wherein C$_{1-6}$alkyl, C$_{2-6}$alkenyl and C$_{1-6}$alkoxy are each optionally substituted with—NR$^{33}$R$^{34}$, aryl, heteroaryl, cycloalkyl, one, two or three halogen atoms, or hydroxy, and wherein aryl and heteroaryl are each optionally substituted with a substituent independently selected from the group consisting of C$_{1-6}$alkyl, C$_{1-6}$alkoxy, C$_{2-6}$alkenyl, C$_{1-6}$alkylthio, —NH$_2$, —NH(C$_{1-6}$)alkyl, —N(C$_{1-6}$)dialkyl, aryl, heteroaryl, aryloxy, heteroaryloxy, one, two or three halogen atoms, hydroxy and nitro;

R$^{31}$, R$^{32}$, R$^{33}$ and R$^{34}$ are substituents independently selected from the group consisting of hydrogen, C$_{1-6}$alkyl and aryl, wherein C$_{1-6}$alkyl is optionally substituted with hydroxy, aryl, —C(═O)C$_{1-4}$alkoxy, NH$_2$, —NH(C$_{1-6}$alkyl), or —N(C$_{1-6}$)dialkyl, and, optionally, R$^{31}$ and R$^{32}$ or R$^{33}$ and R$^{34}$ are each taken together with the atoms to which they are attached to form a ring of five to seven members;

and enantiomers, diastereomers, or pharmaceutically acceptable salts thereof.

2. The compound of claim 1, wherein Ring A is naphthyl and n is 0.

3. The compound of claim 1, wherein R$^1$, R$^2$, R$^3$ and X are each hydrogen and W is O.

4. The compound of claim 1, wherein Y is independently SO$_3$H or P(═O)OR$^5$R$^6$.

5. The compound of claim 4, wherein Y is P(═O)OR$^5$R$^6$.

6. The compound of claim 1, wherein R$^5$ is hydrogen or C$_{1-6}$alkyl.

7. The compound of claim 6, wherein R$^5$ is hydrogen or methyl.

8. The compound of claim 1, wherein R$^6$ is selected from the group consisting of C$_{1-6}$alkyl and hydroxy.

9. The compound of claim 8, wherein R$^6$ is selected from the group consisting of methyl and hydroxy.

10. The compound of claim 1, wherein R$^4$ is one, two or three substituents selected from the group consisting of hydrogen, C$_{1-6}$alkyl, C$_{1-6}$alkoxy, halogen and hydroxy.

11. The compound of claim 10, wherein R$^4$ is one or two or three substituents selected from the group consisting of hydrogen, chlorine, bromine, hydroxy, methyl and methoxy.

12. A compound of Formula (Ia):

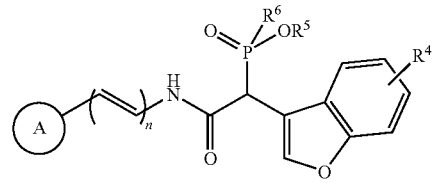

wherein

Ring A is aryl;

n is 0 or 1;

R$^5$ is selected from the group consisting of hydrogen and C$_{1-6}$alkyl;

R$^6$ is selected from the group consisting of C$_{1-8}$alkyl and hydroxy;

R$^4$ is one, two or three substituents selected from the group consisting of hydrogen, C$_{1-6}$alkyl, C$_{1-6}$alkoxy, halogen and hydroxy;

and enantiomers, diastereomers, or pharmaceutically acceptable salts thereof.

13. The compound of claim 12, wherein Ring A is naphthyl and n is 0.

14. The compound of claim 12, wherein $R^5$ is hydrogen or methyl.

15. The compound of claim 12, wherein $R^6$ is selected from the group consisting of methyl and hydroxy.

16. The compound of claim 12, wherein $R^4$ is one or two or three substituents selected from the group consisting of hydrogen, chlorine, bromine, hydroxy, methyl and methoxy.

17. A compound or an enantiomer, diastereomer, or pharmaceutically acceptable salt thereof selected from the group consisting of:

[benzofuran-3-yl-(naphthalen-2-ylcarbamoyl)-methyl]-phosphonic acid,
[(5-methyl-benzofuran-3-yl)-(naphthalen-2-ylcarbamoyl)-methyl]-phosphonic acid,
[(5-methoxy-benzofuran-3-yl)-(naphthalen-2-ylcarbamoyl)-methyl]-phosphonic acid,
[(6-methoxy-benzofuran-3-yl)-(naphthalen-2-ylcarbamoyl)-methyl]-phosphonic acid,
[(5,7-dibromo-benzofuran-3-yl)-(naphthalen-2-ylcarbamoyl)-methyl]-phosphonic acid,
[(5,7-dibromo-6-methyl-benzofuran-3-yl)-(naphthalen-2-ylcarbamoyl)-methyl]-phosphonic acid,
[(5,7-dibromo-6-methoxy-benzofuran-3-yl)-(naphthalen-2-ylcarbamoyl)-methyl]-phosphonic acid,
[(5-chloro-benzofuran-3-yl)-(naphthalen-2-ylcarbamoyl)-methyl]-phosphonic acid,
[(4-hydroxy-benzofuran-3-yl)-(naphthalen-2-ylcarbamoyl)-methyl]-phosphonic acid,
[(5-bromo-benzofuran-3-yl)-(naphthalen-2-ylcarbamoyl)-methyl]-phosphonic acid,
[(7-methoxy-benzofuran-3-yl)-(naphthalen-2-ylcarbamoyl)-methyl]-phosphonic acid,
[(5-hydroxy-benzofuran-3-yl)-(naphthalen-2-ylcarbamoyl)-methyl]-phosphonic acid,
[benzofuran-3-yl-(naphthalen-2-ylcarbamoyl)-methyl]-methyl-phosphinic acid, methyl-[(5-methyl-benzofuran-3-yl)-(naphthalen-2-ylcarbamoyl)-methyl]-phosphinic acid,
[(5-methoxy-benzofuran-3-yl)-(naphthalen-2-ylcarbamoyl)-methyl]-methyl -phosphinic acid,
[(6-methoxy-benzofuran-3-yl)-(naphthalen-2-ylcarbamoyl)-methyl]-methyl -phosphinic acid,
[(5,7-dibromo-benzofuran-3-yl)-(naphthalen-2-ylcarbamoyl)-methyl]-methyl-phosphinic acid,
[(5,7-dibromo-6-methyl-benzofuran-3-yl)-(naphthalen-2-ylcarbamoyl) -methyl]-methyl -phosphinic acid,
[(5,7-dibromo-6-methoxy-benzofuran-3-yl)-(naphthalen-2-ylcarbamoyl)-methyl]-methyl -phosphinic acid,
[(5-chloro-benzofuran-3-yl)-(naphthalen-2-ylcarbamoyl)-methyl]-methyl -phosphinic acid,
[(4-hydroxy-benzofuran-3-yl)-(naphthalen-2-ylcarbamoyl)-methyl]-methyl -phosphinic acid,
[(5-bromo-benzofuran-3-yl)-(naphthalen-2-ylcarbamoyl)-methyl]-methyl -phosphinic acid,
[(7-methoxy-benzofuran-3-yl)-(naphthalen-2-ylcarbamoyl)-methyl]-methyl -phosphinic acid, and
[(5-hydroxy-benzofuran-3-yl)-(naphthalen-2-ylcarbamoyl)-methyl]-methyl -phosphinic acid.

18. A composition comprising the compound of claim 1 and a pharmaceutically acceptable carrier.

19. A composition comprising the compound of claim 12 and a pharmaceutically acceptable carrier.

\* \* \* \* \*